US012698305B2

(12) United States Patent
Cesarman et al.

(10) Patent No.: US 12,698,305 B2
(45) Date of Patent: Aug. 4, 2026

(54) NUCLEOSIDE ANALOGS AND USE THEREOF IN THERAPEUTIC TREATMENT

(71) Applicant: CORNELL UNIVERSITY, Ithaca, NY (US)

(72) Inventors: Ethel Cesarman, Jersey City, NJ (US); Utthara Nayar, Boston, MA (US); J. David Warren, New York, NY (US); Jouliana Sadek, Roosevelt Island, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 265 days.

(21) Appl. No.: 18/525,031

(22) Filed: Nov. 30, 2023

(65) Prior Publication Data

US 2024/0109933 A1 Apr. 4, 2024

Related U.S. Application Data

(62) Division of application No. 16/092,628, filed as application No. PCT/US2017/027590 on Apr. 14, 2017, now abandoned.

(60) Provisional application No. 62/323,637, filed on Apr. 16, 2016.

(51) Int. Cl.

| | |
|---|---|
| ***A61K 31/7076*** | (2006.01) |
| ***A61P 35/00*** | (2006.01) |
| ***C07H 19/16*** | (2006.01) |
| ***C07H 19/167*** | (2006.01) |
| ***C07H 19/20*** | (2006.01) |
| ***C07H 19/213*** | (2006.01) |
| ***C12Q 1/6886*** | (2018.01) |
| ***G01N 33/50*** | (2006.01) |
| ***G01N 33/575*** | (2026.01) |

(52) U.S. Cl.

CPC ......... *C07H 19/16* (2013.01); *A61K 31/7076* (2013.01); *A61P 35/00* (2018.01); *C07H 19/167* (2013.01); *C07H 19/20* (2013.01); *C07H 19/213* (2013.01); *C12Q 1/6886* (2013.01); *G01N 33/5011* (2013.01); *G01N 33/575* (2026.01); *C12Q 2600/106* (2013.01); *C12Q 2600/158* (2013.01); *G01N 2333/912* (2013.01)

(58) Field of Classification Search

USPC ........................................................... 514/45

See application file for complete search history.

(56) References Cited

U.S. PATENT DOCUMENTS

| | | | |
|---|---|---|---|
| 5,185,437 A | 2/1993 | Koszalka et al. |
| 5,773,424 A | 6/1998 | el Kouni et al. |
| 5,792,752 A | 8/1998 | Cho-Chung et al. |
| 7,910,783 B2 | 3/2011 | Voskoboynikov et al. |
| 8,815,827 B2 | 8/2014 | Wald |
| 2010/0210836 A1 | 8/2010 | Bottini et al. |

FOREIGN PATENT DOCUMENTS

| | | | | |
|---|---|---|---|---|
| EP | 2711009 A1 * | 3/2014 | ............. A61P 35/04 |
| WO | 2005120521 A2 | 12/2005 | |
| WO | 2015133491 A1 | 9/2015 | |
| WO | 2017180981 A1 | 10/2017 | |

OTHER PUBLICATIONS

Shamloo et al., Oncotarget, 2019, vol. 10 (No. 68), pp. 7238-7250. (Year: 2019).*

6-Thio Purines—Jena Bioscience, https://www.jenabioscience.com/nucleotides-nucleosides/nucleotides-by-structure/important-structure-motifs/6-thio-purines, Printed from web on Jul. 25, 2023, 3 pages.

Brouwer, C., et al., "Role of 5'-nucleotidase in thiopurine metabolism: enzyme kinetic profile and association with thio-GMP levels in patients with acute lymphoblastic leukemia during 6-mercaptopurine treatment", Clinica Chimica Acta, Received Jan. 5, 2005, Received in revised form Apr. 29, 2005, Accepted May 2, 2005, Available online Jun. 28, 2005, pp. 95-103, 2005, vol. 361.

DataSheet 6-methylthio-IMP, Jena Bioscience, Printed from web on Jun. 25, 2023, 1 page.

Dervieux, T., et al., "Liquid Chromatography-Tandem Mass Spectrometry Analysis of Erythrocyte Thiopurine Nucleotides and Effect of Thiopurine Methyltransferase Gene Variants on These Metabolites in Patients Receiving Azathioprine/6-Mercaptopurine Therapy", Clinical Chemistry, Recieved Mar. 15, 2005, Accepted Aug. 11, 2005, pp. 2074-2084, 51:11.

International Search Report received in PCT/US2017/027590 dated Aug. 2, 2017, 3 pages.

Krenitsky, T.A., et al., "Pyrazolo[3,4-d]pyrimidine ribonucleosides as anticoccidials. 1. Synthesis and activity of some nucleosides of purines and 4-(alkylthio)pyrazolo[3,4-d]pyrimidines", Journal of Medicinal Chemistry, 1982, pp. 32-35, vol. 25(1).

Mizuno, Y., et al., "Nucleotides. II. Syntheses and deblocking of 1-oxido-2-pyridylmethylprotected nucleosides and nucleotides", Journal of Organic Chemistry, Recived Jan. 2, 1974, pp. 1250-1255, vol. 39, No. 9.

Zheng, Q., et al., "Introduction of structural diversity into oligonucleotides containing 6-thioguanine via on-column conjugation", Tetrahedron (2003), Received Nov. 4, 2002, Revised Dec. 23, 2002, Accepted Jan. 23, 2003, pp. 1925-1932, vol. 59.

* cited by examiner

*Primary Examiner* — Traviss C Mcintosh, III

(74) *Attorney, Agent, or Firm* — Scully, Scott, Murphy & Presser, P.C.

(57) ABSTRACT

The present disclosure is directed to novel nucleoside analog compounds and methods for treating diseases characterized by high expression levels of adenosine kinase (ADK).

6 Claims, 18 Drawing Sheets

Compounds

| | | |
|---|---|---|
| A | (3R,4S,5R)-5-(hydroxymethyl)tetrahydrofuran-2,3,4-triol | 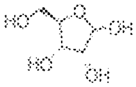 |
| B | 9-((3R,4S,5R)-3,4-dihydroxy-5-(hydroxymethyl)tetrahydrofuran-2-yl)-1H-purin-6(9H)-one | 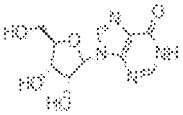 |
| C | (2R,3S,4R)-2-(hydroxymethyl)-5-(6-(methylthio)-9H-purin-9-yl)tetrahydrofuran-3,4-diol | 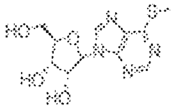 |
| D | (2R,3S,4R)-2-(hydroxymethyl)-5-(6-(4-nitrobenzylthio)-9H-purin-9-yl)tetrahydrofuran-3,4-diol | 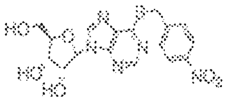 |
| E | ((3aR,4R,6aR)-6-(6-mercapto-9H-purin-9-yl)-2,2-dimethyltetrahydrofuro[3,4-d][1,3]dioxol-4-yl)methanol | 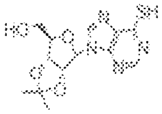 |
| F | (2R,3R,4R)-2-(acetoxymethyl)-5-(6-(methylthio)-9H-purin-9-yl)tetrahydrofuran-3,4-diyl diacetate | 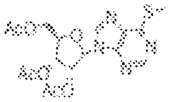 |
| G | ((3aR,4R,6aR)-2,2-dimethyl-6-(6-(methylthio)-9H-purin-9-yl)tetrahydrofuro[3,4-d][1,3]dioxol-4-yl)methanol | 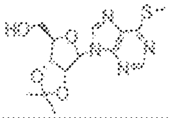 |
| H | (2R,3S,4R)-2-(benzyloxymethyl)-5-(6-(methylthio)-9H-purin-9-yl)tetrahydrofuran-3,4-diol | 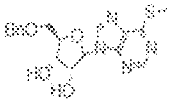 |
| I | 9-((3aR,6R,6aR)-6-(benzyloxymethyl)-2,2-dimethyltetrahydrofuro[3,4-d][1,3]dioxol-4-yl)-6-(methylthio)-9H-purine | 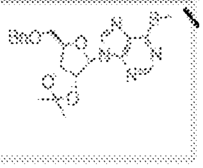 |

Figure 10A

NUCLEOSIDE ANALOGS AND USE THEREOF IN THERAPEUTIC TREATMENT

CROSS REFERENCE TO RELATED APPLICATION

This application claims the benefit of priority from U.S. Provisional Application No. 62/323,637, filed Apr. 16, 2016, the entire contents of which are incorporated herein by reference.

STATEMENT REGARDING FEDERALLY SPONSORED RESEARCH OR DEVELOPMENT

This invention was made with government support under Grant Numbers CA015422, CO012400 & AI007621 awarded by the National Institutes of Health. The Government has certain rights in the invention.

BACKGROUND

The γ-herpesvirus KSHV, also called HHV-8, is the etiologic agent of Kaposi's sarcoma (KS) (Chang Y. et al., *Science.* 1994; 266(5192):1865-9), multicentric Castleman's disease (MCD) (Soulier J. et al., *Blood.* 1995; 86(4): 1276-80.), and primary effusion lymphoma (PEL) (Cesarman E. et al., *N Engl J Med.* 1995; 332(18):1186-91). KS, the most common malignancy in AIDS patients, is a tumor of endothelial origin, while PEL is a rare non-Hodgkin B cell lymphoma that commonly manifests as lymphomatous effusions. Combined antiretroviral therapy has been shown to be effective in some cases of KS, as are other non-curative approaches such as radiation, surgery, and chemotherapy. However, PEL itself remains by large a highly aggressive and intractable disease, with rapid progression to death. Therefore, the need for specific and effective therapeutics for diseases involving KSHV is pressing, albeit challenging due to the latent nature of the virus.

Two broad approaches can be envisioned to identify new strategies for the treatment of virus-associated malignancies to target specific vulnerabilities conferred by viral infection. The first one is to use existing agents that target pathways that are activated by the virus and are essential for tumor cell survival. The advantage of this strategy is the availability of compounds previously tested for other diseases and in clinical use, with documented pharmacological properties. There have been studies on the effectiveness of such commercially available or clinically established pathway inhibitors, such as the NF-κB inhibitor Bay 11-7082 and the Hsp90 inhibitor PU-H71 in PEL cell lines (Sarek G. et al., *J Clin Invest.* 2007; 117(4):1019-28; Nayar U. et al., *Blood.* 2013; 122(16):2837-47; Keller S A. et al., *Blood.* 2006; 107(8):3295-302). However, none of these have been completely effective in mouse models or involved the use of compounds that are already past early phases of clinical trials. A second approach is to identify specific inhibitors of viral proteins, which provides the unique opportunity for very specific and potentially non-toxic therapy. One possible candidate viral oncogene is vFLIP, a viral latent protein encoded by KSHV and expressed in all infected tumor cells. vFLIP is essential for PEL cell survival as demonstrated by RNAi (Guasparri I. et al., *J Exp Med.* 2004; 199(7):993-1003); this effect is mediated by binding of vFLIP to IKKγ and activation of the downstream NF-κB pathway (Liu L. et al, *J Biol Chem.* 2002; 277(16): 13745-51; Field N. et al., *J Cell Sci.* 2003; 116(Pt 18):3721-8). A third approach is to identify inhibitors that are selective to specific stages of cellular differentiation. PEL is a tumor of B cell origin with plasmacytic differentiation, and has features similar to other plasma cells malignancies, as well as adenocarcinomas, that represent malignancies of epithelial origin with cellular differentiation.

SUMMARY OF THE DISCLOSURE

In one aspect, this disclosure provides novel nucleoside analog compounds. In some embodiments, the nucleoside analog compound is a 6-ETI analog having the chemical structure:

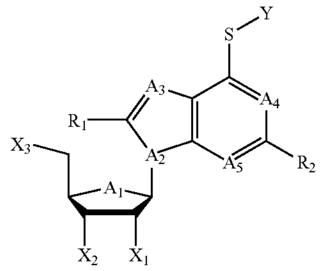

wherein:

$A_1$, $A_2$, $A_3$, $A_4$, $A_5$ are independently a carbon atom or a heteroatom, wherein the heteroatom is B, O, N, or S;

Y is alkyl, heteroalkyl, cycloalkyl, heterocyclic, aryl, heteroaryl, alkylaryl, alkylheteroaryl, alkoxy, aryloxy, heteroalkoxy, or heteroaryloxy;

$R_1$ and $R_2$ are independently hydrogen, halo, amino, $N_3$, alkyl, heteroalkyl, cycloalkyl, heterocyclic, aryl, heteroaryl, alkylaryl, alkylheteroaryl, alkoxy, aryloxy, heteroalkoxy, heteroaryloxy, alkylthio, arylthio, heteroalkylthio, or heteroarylthio;

$X_1$ and $X_2$ are independently hydrogen, hydroxyl, alkyl, heteroalkyl, cycloalkyl, heterocyclic, aryl, heteroaryl, alkylaryl, alkylheteroaryl, alkoxy, aryloxy, heteroalkoxy, heteroaryloxy, alkylthio, arylthio, heteroalkylthio, heteroarylthio, arylsufonyl, araalkylsulfonyl, acyloxy, or aralkyloxy; and $X_3$ is phosphate, hydroxyl, alkyl, heteroalkyl, cycloalkyl, heterocyclic, aryl, heteroaryl, alkylaryl, alkylheteroaryl, aryloxy, heteroalkoxy, heteroaryloxy, alkylthio, arylthio, heteroalkylthio, heteroarylthio, arylsufonyl, araalkylsulfonyl, acyloxy, or aralkyloxy, or $X_1$ and $X_2$ are taken together to form a heterocyclic moiety, wherein the heterocyclic moiety is optionally substituted with alkyl, or $X_2$ and $X_3$ are taken together to form a cyclic monophosphate, or a heterocyclic moiety containing a heteroatom selected from the group consisting of B, N and S, with the proviso that when $X_1$ is hydroxyl, $X_2$ is hydroxyl, then $X_3$ is not hydroxyl, phosphate, or acyloxy.

In another aspect, this disclosure is directed to a method of treating a disease characterized by high expression levels of ADK comprising administration of a nucleoside analog compound.

In some embodiments, the disease being treated is a cancer. In some embodiments, the cancer is a cancer of plasma cell origin, e.g., primary effusion lymphoma (PEL), multiple myeloma (MM) and plasmablastic lymphoma (PBL). In some embodiments, the cancer is adenocarcinoma, e.g., pulmonary adenocarcinoma, adenocarcinoma of the colon, and pancreatic adenocarcinoma. In some embodiments, the disease is associated with Kaposi's Sarcoma Herpes Virus (KSHV), e.g., Kaposi's Sarcoma (KS), multicentric Castleman's Disease (MCD), and primary effusion lymphoma (PEL).

In some embodiments, a nucleoside analog compound being administered has the following chemical structure:

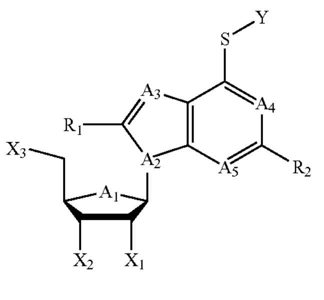

wherein:

- $A_1$, $A_2$, $A_3$, $A_4$, $A_5$ are independently a carbon atom or a heteroatom, wherein the heteroatom is B, O, N, or S;
- Y is alkyl, heteroalkyl, cycloalkyl, heterocyclic, aryl, heteroaryl, alkylaryl, alkylheteroaryl, alkoxy, aryloxy, heteroalkoxy, or heteroaryloxy;
- $R_1$ and $R_2$ are independently hydrogen, halo, amino, $N_3$, alkyl, heteroalkyl, cycloalkyl, heterocyclic, aryl, heteroaryl, alkylaryl, alkylheteroaryl, alkoxy, aryloxy, heteroalkoxy, heteroaryloxy, alkylthio, arylthio, heteroalkylthio, or heteroarylthio; and
- $X_1$, $X_2$, $X_3$ are independently hydrogen, hydroxyl, phosphate, alkyl, heteroalkyl, cycloalkyl, heterocyclic, aryl, heteroaryl, alkylaryl, alkylheteroaryl, alkoxy, aryloxy, heteroalkoxy, heteroaryloxy, alkylthio, arylthio, heteroalkylthio, heteroarylthio, arylsufonyl, araalkylsulfonyl, acyloxy, or aralkyloxy,
- or $X_1$ and $X_2$ are taken together to form a heterocyclic moiety, wherein the heterocyclic moiety is optionally substituted with alkyl,
- or $X_2$ and $X_3$ are taken together to form a cyclic monophosphate, or a heterocyclic moiety containing a heteroatom selected from the group consisting of B, N and S.

In a further aspect, the disclosure is directed to a method of determining whether a cancer is sensitive to treatment with a nucleoside analog compound wherein the nucleoside compound is 6-ETI or a 6-ETI analog. The method includes detecting the expression level of adenosine kinase (ADK) in the cancer; and comparing the detected expression level of ADK in step (a) with a control expression level of ADK, wherein a higher ADK expression level relative to the control expression level indicates responsiveness to treatment with a nucleoside analog compound.

In another aspect, the disclosure is directed to a method of identifying the effectiveness of a nucleoside analog compound in treating cancer characterized by high expression levels of ADK. The method includes providing a 6-ETI-resistant cell line and a 6-ETI-sensitive cell line, wherein 6-ETI-resistant cell line comprises a mutated or deleted ADK gene and the 6-ETI-sensitive cell line comprises a wild type ADK gene; contacting the 6-ETI-resistant and 6-ETI-sensitive cell lines with a candidate nucleoside analog compound; assessing viability of the 6-ETI-resistant and sensitive cell lines; and identifying the candidate nucleoside analog compound as effective in treating cancer characterized by high expression levels of ADK if the candidate nucleoside analog compound decreases the viability of the 6-ETI-sensitive cell line but does not decrease the viability of the 6-ETI-resistant cell line.

Figures 1A, 1B:
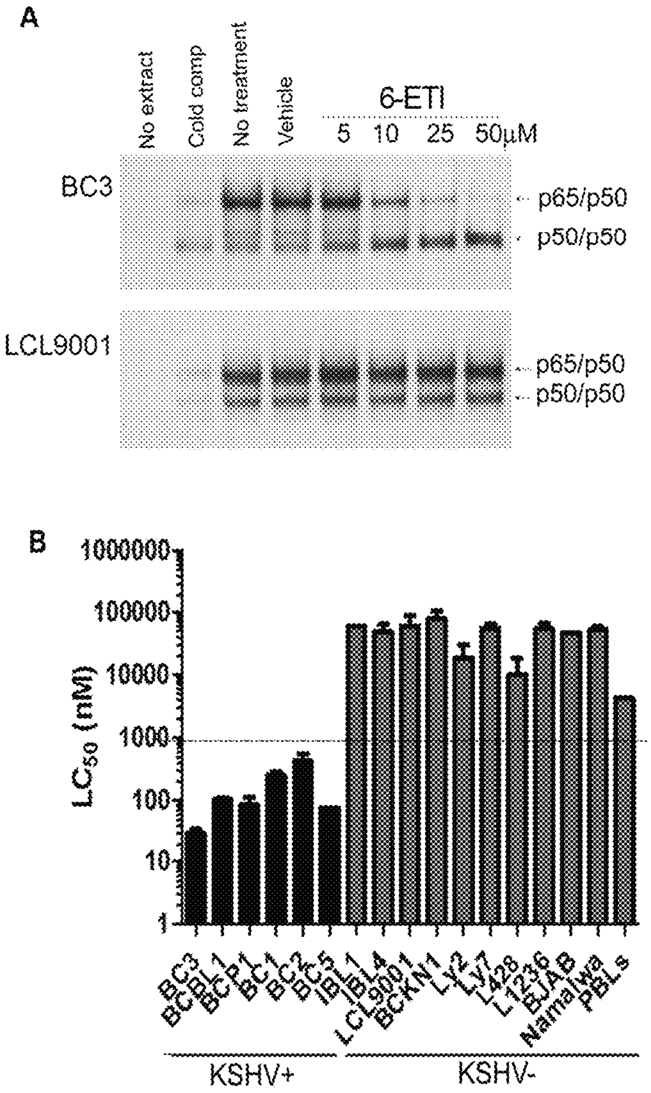
FIGS. 1A-1D. Selection of 6-ETI. (A) BC3 (KSHV+) and LCL9001 (KSHV−) cells were treated for 24 hours with selected doses of NSC39368 (6-ETI), followed by nuclear extraction and EMSA to determine binding to an NF-κB response element. Control lanes include no compound, competition with cold probe, untreated and DMSO-treated samples. Experiment was performed three separate times. A representative blot is shown. (B) A panel of KSHV+ (black bars) and KSHV− (grey bars) cell lines was plated at $1*10^5$ cells/ml in RPMI with 20% FBS with increasing concentrations of 6-ETI, followed by analysis for ATP content by Cell Titer Glo assay at 48 hours. $LC_{50}$s were determined by online $EC_{50}$ software. Results are mean±SEM of at least three independent experiments. (C) BC3 and IBL1 cells plated at $1*10^5$ cells/ml in RPMI with 20% FBS at a range of concentrations of 6-ETI were examined for cell death by Trypan-blue staining-aided cell counts at 48 hours after treatment. Results plotted are mean±SEM of at least three independent experiments. (D) BC3 and IBL1 cells plated at $2*10^5$ cells/ml in RPMI with 20% FBS were treated with DMSO, 500 nM or 5 μM 6-ETI for 48 hours and analyzed by flow cytometry for cell death following staining with Annexin V and 7-AAD. Results are the average of at least two independent experiments (mean±SEM).

NOD-SCID mice randomized into vehicle (n=10), low dose (150 mg/kg/day) (n=10) and high dose (300 mg/kg/day)) (n=10) treatment groups after BC3 NFRen-#3 tumor engraftment were followed by weighing and luciferase imaging in vivo to follow tumor progression. Mice in both treatment groups were treated for two separate 9-day intervals as indicated. Representative results from the first trial of two are shown. (C) Quantitation of tumor burden by bioluminescence imaging from two independent trials. Data is shown through day 41. Statistical analysis was performed using one-way ANOVA ($p=0.0032$ at day 11 post-treatment, **$p\leq0.05$. Kaplan-Meier with (D) progression-free (n=22) and (E) overall (n=30) survival analysis was performed on all mice from both trials, and the results shown color-coded by treatment group. In the progression-free survival curve (panel D) the low (n=8) and high (n=4) dose treatment arms showed complete overlap, as by day 100 all live mice were tumor free, and none had died of tumor. The difference in survival curves was analyzed by Log-rank (Mantel-Cox) test ($p<0.0001$).

Figure 4A:
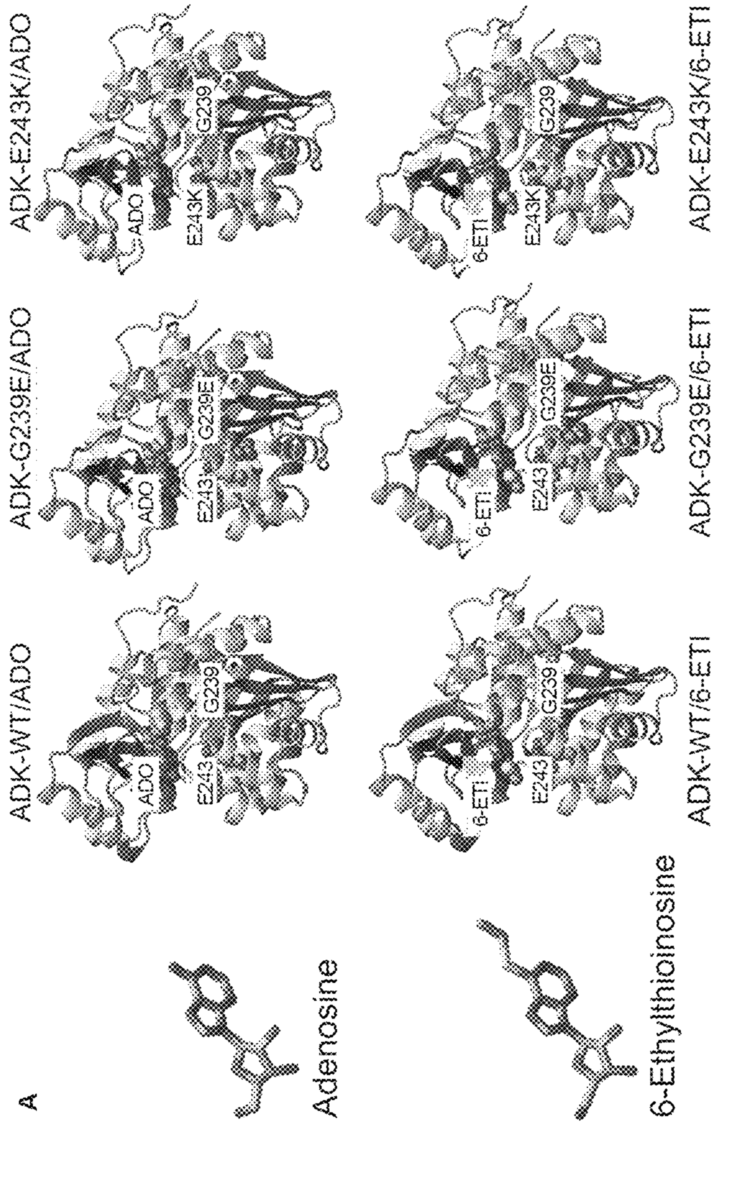
Figures 4B, 4C:
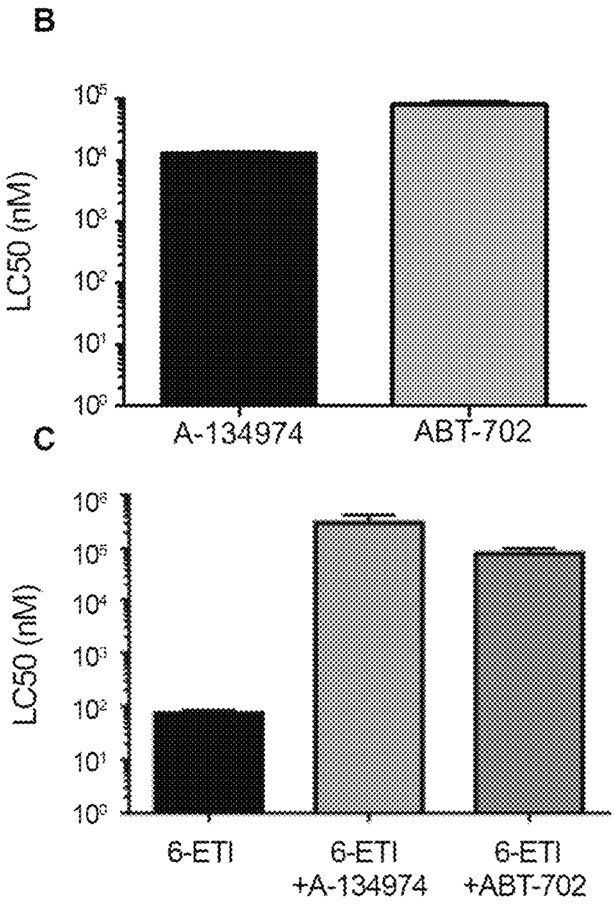

FIGS. 4A-4C. Adenosine kinase is required for 6-ETI activation. (A) Figure indicates locations of independent recurrent mutations G239E and E243K on ADK, discovered by SNP calling on RNASeq data from 6-ETI-resistant clones. Schrödinger's Maestro was used to model ADK binding to Adenosine (top panel), and postulated binding to 6-ETI (bottom panel). (B) BC3 cells treated at a range of concentrations of A-134974 or ABT-702 were analyzed by Cell Titer-Glo assay for viability at 48 hours. Results are shown as the mean±SEM of at least three independent experiments where $LC_{50}$s were determined using online $EC_{50}$ software. (C) 6-ETI viability dose curves were set up on BC3 cells pretreated with 1 μM ADK inhibitors A-134974 and ABT-702 or DMSO (–), followed by treatment with 6-ETI. The fold increases in 6-ETI $LC_{50}$s are shown via bar graph, representing the mean±SEM at least three independent experiments.

FIGS. 5A-5D. Adenosine kinase levels determine sensitivity to 6-ETI. (A) A panel of KSHV+ and KSHV– lymphoma cell lines were plated at viability assay conditions (i.e., $1*10^5$ cells/ml in RPMI with 20% FBS), and whole cell extracts obtained at 24 hours examined for ADK levels by western blotting. GAPDH was used as a loading control. Results shown are representative of more than three independent experiments. (B) Successful lentiviral shRNA-mediated knock down of ADK in a pancreatic adenocarcinoma PA-Tu-8988T cell line was examined by western blot using an ADK antibody. A representative blot of three independent experiments is shown. 6-ETI viability assays at 24 hrs were performed on the knockdown cell line compared to control. $LC_{50}$ graphed is the average of five independent experiments (mean±SEM). Statistical analysis was performed using Mann-Whitney unpaired test ($p=0.0079$, **$p\leq0.05$). (C) ADK normally phosphorylates adenosine to convert it into adenosine monophosphate (AMP) and similarly adds a phosphate from ATP into 6-ETI to convert it into p6-ETI. (D) PEL cell lines BC3 and BC2 and DLBCL cell line IBL1 were treated with increasing concentrations of 6-ETI and phospho-6ETI for 48 hrs. Results plotted are the average of four independent experiments (mean±SEM). Statistical analysis was performed using Mann-Whitney unpaired test ($p=0.0317$, *$p\leq0.05$).

FIGS. 6A-6E. Expression of ADK and sensitivity to 6-ETI in plasma cell tumors. (A) BC3 cells ADK expression was evaluated by immunohistochemistry in the BC3 cell line, hyperplastic tonsils and PEL, MM and PBL primary tumors (original magnification: 60×). Insert: In the image of a tonsil section, a positive cell with morphological features of a plasma cell is enlarged. Two-color immunohistochemistry showing a high power image of plasma cells expressing both ADK and CD138. (B) $LC_{50}$s for multiple myeloma cell lines treated with 6-ETI for 48 hrs were determined by CellTiter-Glo assay. BC3 was used as a positive control and IBL1 as a negative control for drug sensitivity. Shown is the mean±SEM of two independent experiments, where each condition was performed in duplicate in each experiment. (C) U266 cells were treated with DMSO or 5 μM of 6-ETI for 24 hrs then labeled with 10 μM EdU for 2 hrs. EdU incorporation into the newly synthesized DNA was visualized using click-iT EdU assay. The immunofluorescence images are representative of two independent experiments. (D) Multiple myeloma patient specimens (n=9) were treated with increasing concentrations of 6-ETI ex-vivo, followed by analysis for ATP content by Cell Titer Glo assay at 24 hours. $LC_{50}$s were determined using Graphpad prism. (E) Flow cytometry analysis showing the number of normal plasma cells isolated from human tonsils (CD19–, CD138+) before and after 6-ETI treatment. Data is representative of two independent experiments.

FIGS. 7A-7D. 6-ETI inhibits tumor growth in a disseminated multiple myeloma mouse model. (A) A schematic of engraftment of CAG-luc multiple myeloma cell line into NOD-SCID mice and treatment with 6-ETI is shown. (B) When tumors engrafted (at day 8), mice were injected intraperitoneally with vehicle (7 mice on the left) or 6-ETI (8 mice to the right) for 9 days, at 200 mg/kg/day and tumor progression was monitored using in vivo luciferase imaging. (C) Bioluminescence representing tumor burden after 20 days of follow up in the vehicle (blue line) versus 6-ETI treated group (red line) is indicated. Statistical analysis was performed using unpaired t-test ($p=0.0076$ at day 20 post-treatment and $p<0.05$ at other time points indicated by *). (D) Kaplan-Meier survival analysis was performed on all mice, and the results are color-coded by treatment group. The difference in survival curves was analyzed by Log-rank (Mantel-Cox) test ($p=0.0010$).

Figures 8A, 8B:
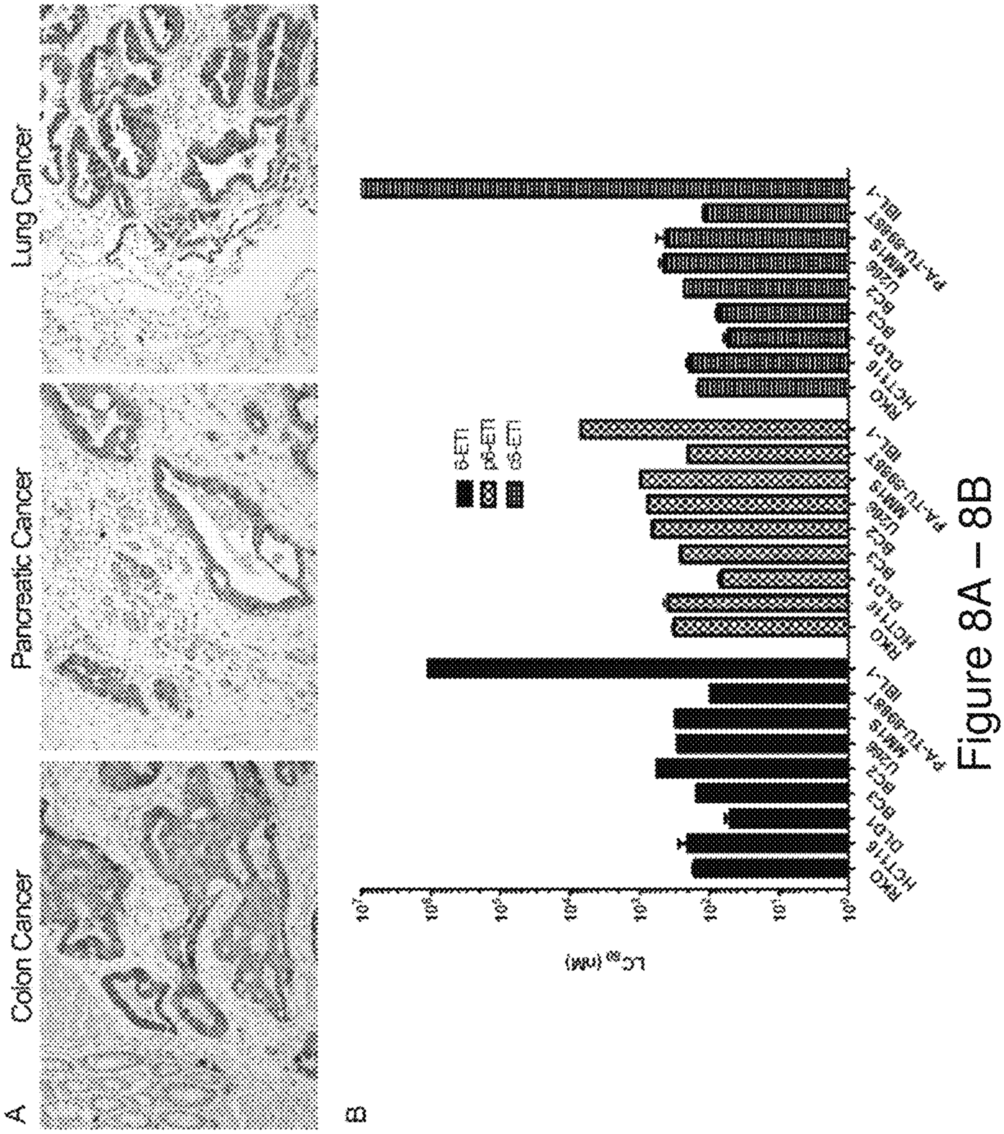

FIG. 8A-8B. ADK expression and 6-ETI sensitivity in adenocarcinomas. (A) ADK is expressed is pancreatic, lung and colon adenocarcinomas (original magnification 20×). (B) Cell lines corresponding to these cancers are sensitive to treatment with 6-ETI, p6-ETI and c6-ETI with LC50s in the nanomolar range. RKO, HCT116 and DLD1 are colon cancer lines, BC3 and BC2 are PEL cell lines, U266 and MM1s are multiple myeloma, PA-TU-8988T is a pancreatic cancer line. IBL1 is a lymphoma cell line with low ADK levels and largely resistant to 6-ETI used as a control.

Figure 9:
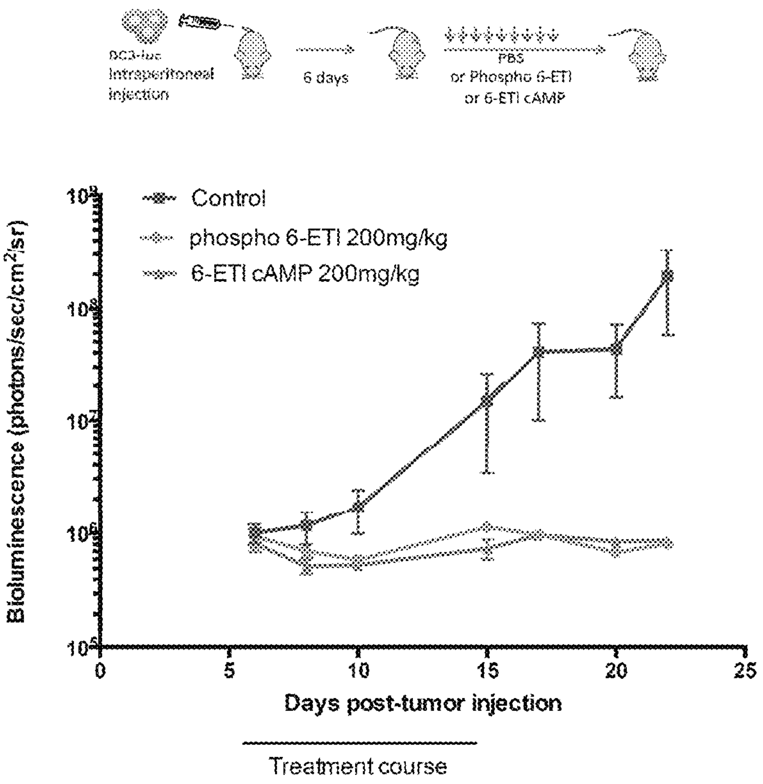

FIG. 9. p6-ETI and 6-ETI cAMP are effective in an PEL xenograft model. Mice were inoculated with PEL cell lines with a luciferase tracer and in vivo imaging was performed to monitor tumor growth. Cohorts of 5 mice were treated with vehicle, p6-ETI or 6-ETI cAMP as indicated. Briefly, BC3-luc reporter cell line was engrafted in NOD-SCID mice. 6 days post-tumor injection, mice we were randomized and treated with vehicle, or 6-ETI derivatives (phospho-6ETI 200 mg/kg and 6-ETI cAMP 200 mg/kg) for 9 days. Tumor progression was monitored using in vivo luciferase imaging. Bioluminescence representing tumor burden 22 days post-engraftment in the vehicle (square solid line) versus phospho 6-ETI treated group (circle solid line) and is 6-ETIcAMP treated group (triangle solid line) is indicated. Statistical analysis was performed using Mann-Whitney test ($p=0.0012$ comparing vehicle and phospho 6-ETI $p\leq0.05$ and $p=0.0006$ comparing vehicle and 6-ETI cAMP, *$p\leq0.05$).

Figure 10B:
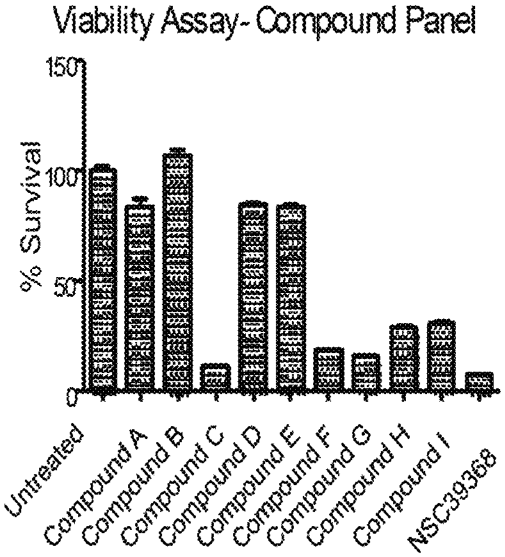

FIGS. 10A-10B. Structure Activity Relationship (SAR) of 6-ETI analogs. (A) The list of 6-ETI analogs used in the viability assay in FIG. 10B. (B) BC3 cells were plated at $5*10^5$ cells/ml, and treated with the 6-ETI related compounds listed in FIG. 10A at 25 μM or with NSC39368 (6-ETI) at 25 μM for 24 hours. Compounds C, F, G, H and I demonstrated tumor inhibiting activity on BC3 cells.

Figure 11:
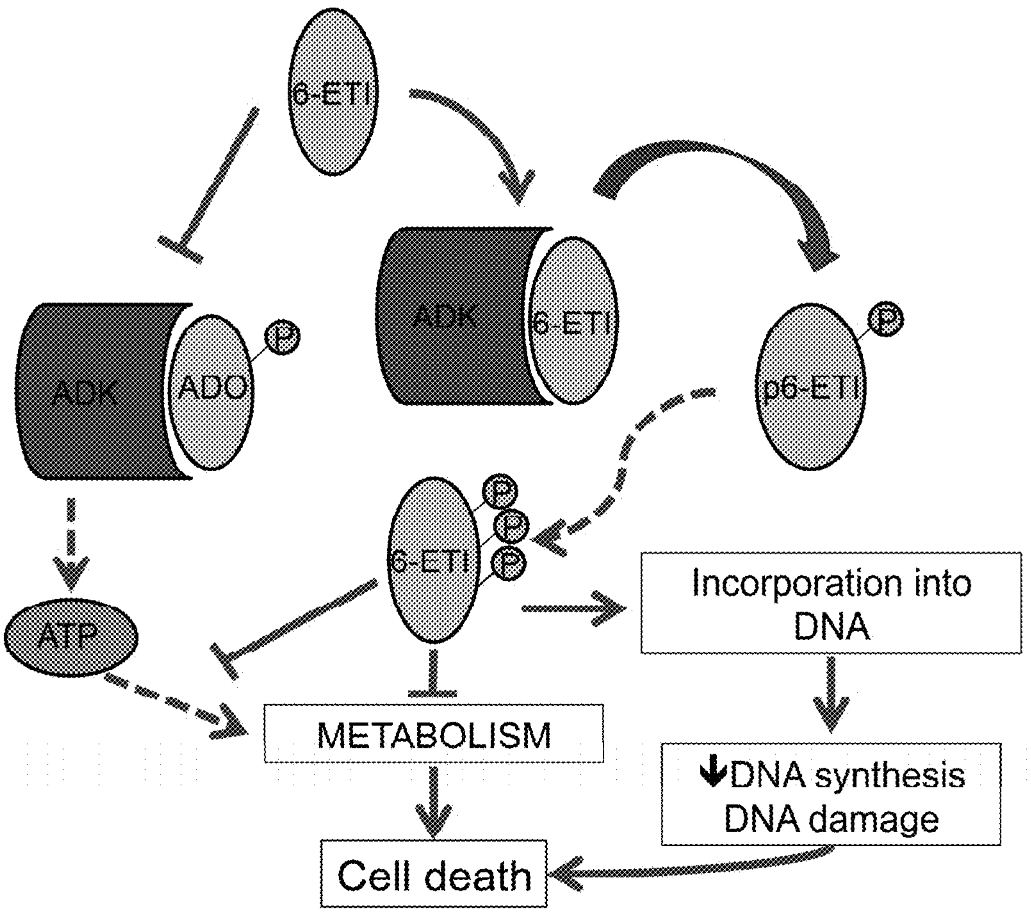

FIG. 11. Model for 6-ETI's mechanism of action. 6-ETI competes with adenosine (ADO) and other nucleosides for binding to and phosphorylation by ADK, which inhibits ATP-dependent processes. This also allows 6-ETI to be phosphorylated and activated by ADK, with subsequent phosphorylation steps that allow the compound to be incorporated into DNA and possibly RNA, leading to DNA synthesis inhibition, DNA damage response, and cell death.

DETAILED DESCRIPTION

This disclosure is directed to novel nucleoside analogs that share structural features with 6-ETI. The disclosure is also directed to therapeutic methods based on the use of nucleoside analogs, including 6-ETI and analogs thereof, in the treatment of conditions characterized by high expression levels of Adenosine Kinase (ADK).

Novel Nucleoside Analogs

In one aspect, this disclosure is directed to nucleoside analog compounds that are 6-ETI analogs.

The term "analog" refers to a chemical compound that is similar in structure to a reference compound, but differs from the reference compound in at least one atom or a group.

The compound 6-ETI (i.e., 6-(Ethylthioinosine) has the following structure:

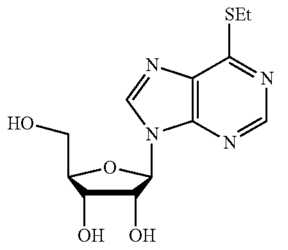

6-ETI

In some embodiments, a 6-ETI analog has the following chemical structure:

Formula (I)

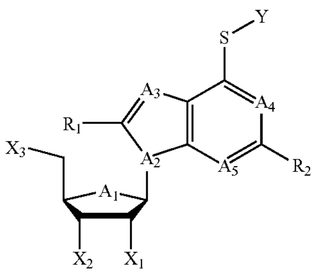

wherein:

$A_1$, $A_2$, $A_3$, $A_4$, $A_5$ are independently a carbon atom or a heteroatom, wherein the heteroatom is B, O, N, or S;

Y is alkyl, heteroalkyl, cycloalkyl, heterocyclic, aryl, heteroaryl, alkylaryl, alkylheteroaryl, alkoxy, aryloxy, heteroalkoxy, or heteroaryloxy;

$R_1$ and $R_2$ are independently hydrogen, halo, amino, $N_3$, alkyl, heteroalkyl, cycloalkyl, heterocyclic, aryl, heteroaryl, alkylaryl, alkylheteroaryl, alkoxy, aryloxy, heteroalkoxy, heteroaryloxy, alkylthio, arylthio, heteroalkylthio, or heteroarylthio;

$X_1$ and $X_2$ are independently hydrogen, hydroxyl, alkyl, heteroalkyl, cycloalkyl, heterocyclic, aryl, heteroaryl, alkylaryl, alkylheteroaryl, alkoxy, aryloxy, heteroalkoxy, heteroaryloxy, alkylthio, arylthio, heteroalkylthio, heteroarylthio, arylsufonyl, araalkylsulfonyl, acyloxy, or aralkyloxy; and $X_3$ is phosphate, hydroxyl, alkyl, heteroalkyl, cycloalkyl, heterocyclic, aryl, heteroaryl, alkylaryl, alkylheteroaryl, aryloxy, heteroalkoxy, heteroaryloxy, alkylthio, arylthio, heteroalkylthio, heteroarylthio, arylsufonyl, araalkylsulfonyl, acyloxy, or aralkyloxy, or $X_1$ and $X_2$ are taken together to form a heterocyclic moiety, wherein the heterocyclic moiety is optionally substituted with alkyl, or $X_2$ and $X_3$ are taken together to form a cyclic monophosphate, or a heterocyclic moiety containing a heteroatom selected from the group consisting of B, N and S, with the proviso that when $X_1$ is hydroxyl, $X_2$ is hydroxyl, then $X_3$ is not hydroxyl, phosphate, or acyloxy.

In some embodiments, $X_1$ and $X_2$ are both hydroxyl groups. In other embodiments, $X_1$ is hydrogen, and $X_2$ is a hydroxyl group.

In certain embodiments, a 6-ETI analog has a chemical structure of Formula (I), wherein $A_1$ is O;

$A_2$, $A_3$, $A_4$ and $A_5$ are independently N;

Y is alkyl;

$R_1$ and $R_2$ are independently H;

$X_1$ and $X_2$ are independently acyloxy, or $X_1$ and $X_2$ are taken together to form a heterocyclic moiety, wherein the heterocyclic moiety is optionally substituted with alkyl; and $X_3$ is hydroxyl, acyloxy, or aralkyloxy.

In a specific embodiment, a 6-ETI analog has the following chemical structure:

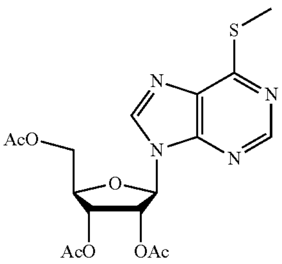

In another specific embodiment, a 6-ETI analog has the following chemical structure:

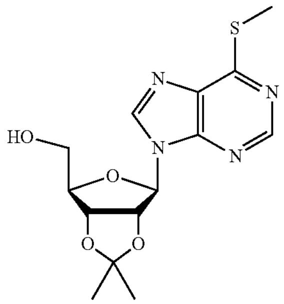

In still another specific embodiment, a 6-ETI analog has the following chemical structure:

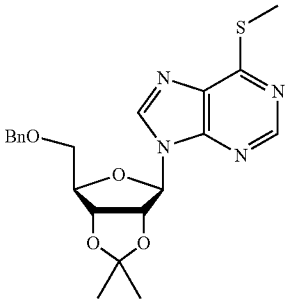

In some embodiments, a 6-ETI analog has a chemical structure of Formula (I), wherein:

$A_1$ is O;

$A_2$, $A_3$, $A_4$ and $A_5$ are independently N;

Y is alkyl;

$R_1$ and $R_2$ are independently H;

$X_1$ and $X_2$ are independently hydroxyl; and $X_3$ is aralkyloxy.

In a specific embodiment, a 6-ETI analog has the following chemical structure:

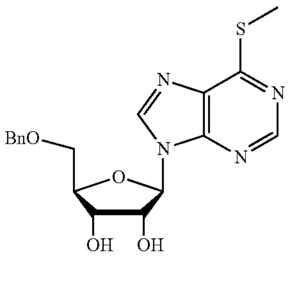

In some embodiments, a 6-ETI analog has a chemical structure of Formula (I), wherein $A_1$ is O;

$A_2$, $A_3$, $A_4$ and $A_5$ are independently N;

Y is alkyl;

$R_1$ and $R_2$ are independently H;

$X_1$ is OH; and $X_2$ and $X_3$ are taken together to form a cyclic monophosphate.

In a specific embodiment, a 6-ETI analog has the following chemical structure:

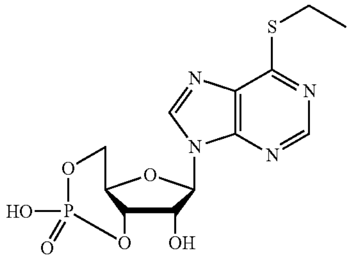

In some embodiments, a 6-ETI analog has the following chemical structure:

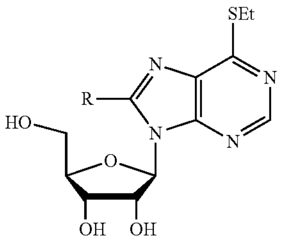

wherein R is Cl, $NH_2$, Br or $N_3$.

Methods of Therapeutic Treatment

In another aspect, this disclosure is directed to therapeutic methods based on the use of nucleoside analogs, including 6-ETI and analogs thereof, in the treatment of conditions or diseases, such as conditions characterized by high expression levels of ADK.

Diseases and Conditions

The phrase "characterized by high expression levels of ADK" when referring to a condition or disease is meant that the expression level of ADK in the cells or tissues underlying the disease or condition (i.e., the cancerous cells or tissue) is abnormally high, i.e., substantially higher as compared to the cells or tissues of a healthy control subject. By "substantially higher" is meant at least 20%, 30%, 40%, 50%, 60%, 70%, 80%, 90%, 100% or greater, as compared to the level in a healthy control subject. The expression levels can be either the levels of mRNA or the levels of protein.

In some embodiments, a subject is first examined to determine and confirm the high expression levels of ADK in relevant cells or tissues prior to treatment. In other embodiments, the subject has been diagnosed through other means with a disease or condition that is known to have characteristic high expression levels of ADK, and therefore it is not necessary to examine the subject again for its expression levels of ADK prior to treatment.

In some embodiments, the disease characterized by high expression levels of ADK is a cancer. The cancer can be a primary cancer, or a metastatic cancer.

In one embodiment, the cancer is a cancer of plasma cell origin. In a specific embodiment, the cancer is primary effusion lymphoma (PEL), multiple myeloma (MM) or plasmablastic lymphoma (PBL).

In one embodiment, the cancer is an adenocarcinoma. In a specific embodiment, the adenocarcinoma is an adenocarcinoma of the lung (pulmonary adenocarcinoma), an adenocarcinoma of the colon, an adenocarcinoma of the pancreas (pancreatic adenocarcinoma), a cholangiocarcinoma (bile duct cancer), breast adenocarcinoma, vaginal adenocarcinoma, thyroid cancer, or stomach cancer.

The term "adenocarcinoma", as used herein, relates to a malignant neoplasm of epithelial cells. Typically, adenocarcinoma is a cancer that originates in glandular tissue. This tissue is part of a more general type of tissue known as epithelial tissue. Epithelial tissue includes skin, glands and a variety of other tissue lining and/or surrounding the cavities and organs of the body. Embryologically, the epithelium is derived from ectoderm, endoderm and mesoderm. In order to be classified as adenocarcinoma, the cells do not necessarily need to be part of a gland, as long as the cells have secretory properties. Hence, adenocarcinomas are also often referred to as "glandular cancer" or "glandular carcinoma". An adenocarcinoma can occur in some higher mammals, including humans. Highly differentiated adenocarcinomas tend to resemble the glandular tissue that they are derived from, while poorly differentiated may not. Traditionally, a pathologist can verify whether a tumor is an adenocarcinoma or some other type of cancer by staining the cells from a biopsy.

In one embodiment, the disease characterized by high expression levels of ADK is a disease associated with the γ-herpesvirus KSHV (Kaposi's sarcoma-associated herpesvirus). In a specific embodiment, the KSV-associated disease is selected from the group consisting of Kaposi's Sarcoma (KS), multicentric Castleman's Disease (MCD) and primary effusion lymphoma (PEL).

As used herein, the term "treatment" or "treating" in reference to a disease or condition means reducing, ameliorating or eliminating the symptoms, or slowing down the progression or development. Where the disease is cancer, "treating cancer" means reducing growth of cancerous cells, reducing or preventing metastasis, causing a regression in the size of an existing tumor or metastasis, eradicating an existing tumor or metastasis, and/or preventing the occurrence of additional metastasis.

Nucleoside Analogs for Use in Therapeutic Treatment

In some embodiments, a nucleoside analog suitable for use in the present methods is a compound that depends on the activity of ADK for activation, including 6-ETI and analogs thereof. The term "activation", as used herein, refers to phosphorylation by ADK and the subsequent formation of the triphosphorylated compound upon further phosphorylation by cellular kinases. Triphosphorylated forms are believed to be the active inhibitor of DNA synthesis.

In some embodiments, a nucleoside analog compound suitable for use in the present methods has the following chemical structure:

Formula (I)

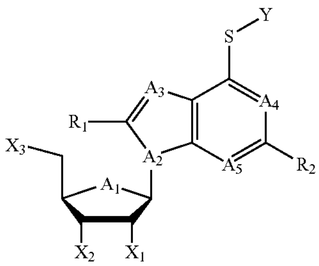

wherein:

$A_1$, $A_2$, $A_3$, $A_4$, $A_5$ are independently a carbon atom or a heteroatom, wherein the heteroatom is B, O, N, or S;

Y is alkyl, heteroalkyl, cycloalkyl, heterocyclic, aryl, heteroaryl, alkylaryl, alkylheteroaryl, alkoxy, aryloxy, heteroalkoxy, or heteroaryloxy;

$R_1$ and $R_2$ are independently hydrogen, halo, amino, $N_3$, alkyl, heteroalkyl, cycloalkyl, heterocyclic, aryl, heteroaryl, alkylaryl, alkylheteroaryl, alkoxy, aryloxy, heteroalkoxy, heteroaryloxy, alkylthio, arylthio, heteroalkylthio, or heteroarylthio; and $X_1$, $X_2$, $X_3$ are independently hydrogen, hydroxyl, phosphate, alkyl, heteroalkyl, cycloalkyl, heterocyclic, aryl, heteroaryl, alkylaryl, alkylheteroaryl, alkoxy, aryloxy, heteroalkoxy, heteroaryloxy, alkylthio, arylthio, heteroalkylthio, heteroarylthio, arylsufonyl, araalkylsulfonyl, acyloxy, or aralkyloxy, or $X_1$ and $X_2$ are taken together to form a heterocyclic moiety, wherein the heterocyclic moiety is optionally substituted with alkyl, or $X_2$ and $X_3$ are taken together to form a cyclic monophosphate, or a heterocyclic moiety containing a heteroatom selected from the group consisting of B, N and S.

In some embodiments, a nucleoside analog compound suitable for use in the present methods has a chemical structure of Formula (II), wherein:

$A_1$ is O;

$A_2$, $A_3$, $A_4$ and $A_5$ are independently N;

Y is alkyl;

$R_1$ is H, Cl, $NH_2$, Br or $N_3$;

$R_2$ is H; and $X_1$, $X_2$ and $X_3$ are independently hydroxyl, phosphate, acyloxy, or aralkyloxy, or $X_1$ and $X_2$ are taken together to form a heterocyclic moiety, wherein the heterocyclic moiety is optionally substituted with alkyl, or $X_2$ and $X_3$ are taken together to form cyclic monophosphate.

In some embodiments, a nucleoside analog is a 6-ETI analog having a chemical structure of Formula (I), wherein:

$A_1$, $A_2$, $A_3$, $A_4$, $A_5$ are independently a carbon atom or a heteroatom, wherein the heteroatom is B, O, N, or S;

Y is alkyl, heteroalkyl, cycloalkyl, heterocyclic, aryl, heteroaryl, alkylaryl, alkylheteroaryl, alkoxy, aryloxy, heteroalkoxy, or heteroaryloxy;

$R_1$ and $R_2$ are independently hydrogen, halo, amino, $N_3$, alkyl, heteroalkyl, cycloalkyl, heterocyclic, aryl, heteroaryl, alkylaryl, alkylheteroaryl, alkoxy, aryloxy, heteroalkoxy, heteroaryloxy, alkylthio, arylthio, heteroalkylthio, or heteroarylthio;

$X_1$ and $X_2$ are independently hydrogen, hydroxyl, alkyl, heteroalkyl, cycloalkyl, heterocyclic, aryl, heteroaryl, alkylaryl, alkylheteroaryl, alkoxy, aryloxy, heteroalkoxy, heteroaryloxy, alkylthio, arylthio, heteroalkylthio, heteroarylthio, arylsufonyl, araalkylsulfonyl, acyloxy, or aralkyloxy; and $X_3$ is phosphate, hydroxyl, alkyl, heteroalkyl, cycloalkyl, heterocyclic, aryl, heteroaryl, alkylaryl, alkylheteroaryl, aryloxy, heteroalkoxy, heteroaryloxy, alkylthio, arylthio, heteroalkylthio, heteroarylthio, arylsufonyl, araalkylsulfonyl, acyloxy, or aralkyloxy;

or $X_1$ and $X_2$ are taken together to form a heterocyclic moiety, wherein the heterocyclic moiety is optionally substituted with alkyl, or $X_2$ and $X_3$ are taken together to form a cyclic monophosphate, or a heterocyclic moiety containing a heteroatom selected from the group consisting of B, N and S, with the proviso that when $X_1$ is hydroxyl, $X_2$ is hydroxyl, then $X_3$ is not hydroxyl, phosphate, or acyloxy.

In some embodiments, $X_1$ and $X_2$ are both hydroxyl groups. In other embodiments, $X_1$ is hydrogen, and $X_2$ is a hydroxyl group.

In certain embodiments, a nucleoside analog is a 6-ETI analog having a chemical structure of Formula (I), wherein $A_1$ is O;

$A_2$, $A_3$, $A_4$ and $A_5$ are independently N;

Y is alkyl;

$R_1$ and $R_2$ are independently H;

$X_1$ and $X_2$ are independently acyloxy, or $X_1$ and $X_2$ are taken together to form a heterocyclic moiety, wherein the heterocyclic moiety is optionally substituted with alkyl; and $X_3$ is hydroxyl, acyloxy, or aralkyloxy.

In some embodiments, a nucleoside analog is a 6-ETI analog having a chemical structure of Formula (I), wherein $A_1$ is O;

$A_2$, $A_3$, $A_4$ and $A_5$ are independently N;

Y is alkyl;

$R_1$ and $R_2$ are independently H;

$X_1$ and $X_2$ are independently hydroxyl; and $X_3$ is aralkyloxy.

In some embodiments, a nucleoside analog is a 6-ETI analog having a chemical structure of Formula (I), wherein $A_1$ is O;

$A_2$, $A_3$, $A_4$ and $A_5$ are independently N;

Y is alkyl;

$R_1$ and $R_2$ are independently H;

$X_1$ is OH; and $X_2$ and $X_3$ are taken together to form a cyclic monophosphate.

In specific embodiments, a nucleoside analog has a chemical structure selected from the following groups:

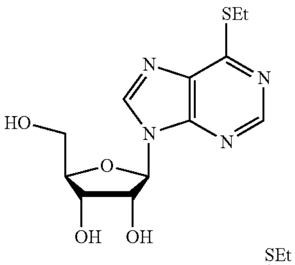

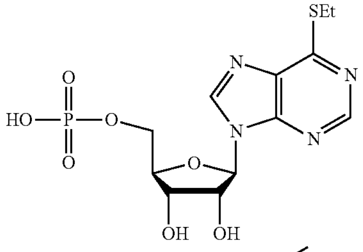

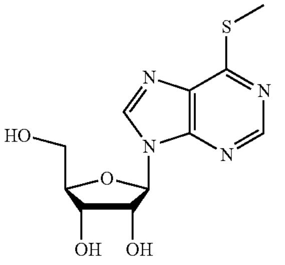

-continued

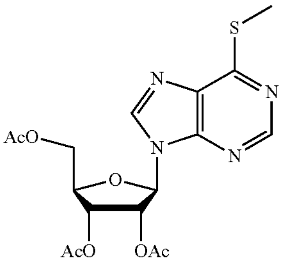

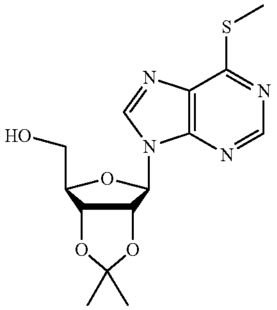

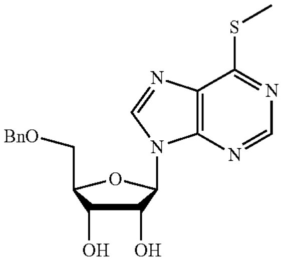

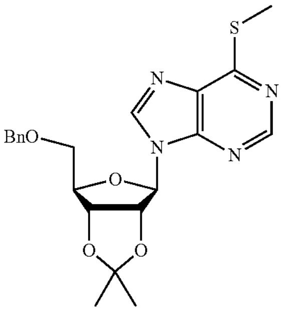

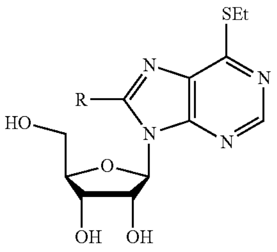

wherein R is Cl, $NH_2$, Br or $N_3$; and

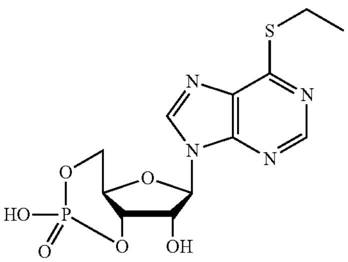

Formulations and Pharmaceutical Compositions

In some embodiments, pharmaceutically acceptable salts of a nucleoside analog compound described herein are also provided.

The term "pharmaceutically acceptable salts" of a compound as used herein, refers to pharmaceutically acceptable organic or inorganic salts of the compound. Exemplary salts include, but are not limited to, sulphate, citrate, acetate, oxalate, chloride, bromide, iodide, nitrate, bisulfate, phosphate, acid phosphate, isonicotinate, lactate, salycilate, acid citrate, tartrate, oleate, tannate, pantothenate, bitartrate, ascorbate, succinat, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate salts. A pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or more counter ion. Chemical modification of a pharmaceutical compound into a salt is a technique well known to pharmaceutical chemists to obtain improved physical and chemical stability, hygroscopicity, flowability and solubility of compounds.

In some embodiments, tautomeric forms of a nucleoside analog compound described herein are also encompassed in this disclosure.

The term "tautomer" or "tautomeric form" refers to structural isomer of different energies which are interconvertible via a low energy barrier. For example, proton tautomers (also known as prototropic tautomers) include interconversion via migration of a proton, such as keto-enol and imine-enamine isomerizations. Valence tautomers include interconversions by reorganization of some of the bonding electrons.

The phrase "pharmaceutically acceptable" indicates that the substance or composition must be compatible chemically and/or toxicologically, with the other ingredients comprising a formulation, and/or the mammal being treated therewith.

In some embodiments, a nucleoside analog compound described herein (e.g., 6-ETI or analog thereof) can be combined with a pharmaceutically acceptable carrier to provide a pharmaceutical composition suitable for administration.

For the purposes of this disclosure, "pharmaceutically acceptable carriers" means any of the standard pharmaceutical carriers. Examples of suitable carriers are well known in the art and may include, but are not limited to, any of the standard pharmaceutical carriers such as a phosphate buffered saline solution and various wetting agents. Other carriers may include additives used in tablets, granules and capsules, and the like. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

A nucleoside analog can be admixed with a pharmaceutically acceptable carrier to make a a pharmaceutical preparation in any conventional form including, inter alia, a solid form such as tablets, capsules (e.g. hard or soft gelatin capsules), pills, cachets, powders, granules, and the like; a liquid form such as solutions, suspensions; or in micronized powders, sprays, aerosols and the like.

Administration and Dosage Amount

In some embodiments, a nucleoside analog compound disclosed herein can be administered by any of the conventional routes of administration, including but not limited to oral, nasal, or parenteral (including e.g., subcutaneous, intramuscular, transcutaneous, intradermal, intraperitoneal, intraocular, and intravenous) route.

In some embodiments, a nucleoside analog compound is administered to a subject at a dose between 0.2 mg/kg and 300 mg/kg, depending on the particular compound used and the route of administration chosen. In other embodiments, a nucleoside analog compound is administered at a dose about 0.2 mg/kg, 0.5 mg/kg, 8 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 150 mg/kg, 175 mg/kg, 200 mg/kg, 250 mg/kg, 275 mg/kg or 300 mg/kg.

In some embodiments, a nucleoside analog compound is administered to a patient in need thereof every day. In some embodiments, a nucleoside analog compound is administered intermittently every 2, 3, 4, 5, or 6 days, or every week, every 2, 3, or 4 weeks, as appropriate.

Methods of Diagnosis/Prognosis

In a further aspect, this disclosure is directed to a method of determining whether a disease (e.g., cancer) is sensitive to treatment with a nucleoside analog compound disclosed hereinabove (e.g., 6-ETI or analog thereof).

According to this method, the expression level of adenosine kinase (ADK) in the relevant cells or tissues underlying the disease is detected and compared to a control expression level of ADK (e.g., the expression level of ADK in cells or tissues of the same origin from a healthy control subject), wherein a substantially higher ADK expression level relative to the control expression level indicates responsiveness to treatment with a nucleoside analog compound disclosed hereinabove (e.g., 6-ETI or analog thereof).

In some embodiments, the ADK expression level is determined at the protein level or the RNA level.

In some embodiments, the ADK expression level is determined by a technique selected from the group consisting of immunoblotting, immunohistochemistry, Reverse transcription polymerase chain reaction (RT-PCR), and RNA Sequencing (RNA-Seq).

Methods of Screening for Inhibitors of Cancer

In a further aspect, this disclosure is directed to a method of identifying a nucleoside analog inhibitor of cancer characterized by high expression levels of ADK.

According to this method, a 6-ETI-resistant cell line and a 6-ETI-sensitive cell line are provided, wherein 6-ETI-resistant cell line comprises a mutated or deleted ADK gene (such that the cell line substantially has no ADK activity) and the 6-ETI-sensitive cell line comprises a wild type ADK gene. The two cell lines are contacted with a candidate nucleoside analog compound, and their viabilities are assessed. The candidate nucleoside analog compound is identified as an inhibitor of cancer characterized by high expression levels of ADK if the candidate nucleoside analog compound decreases the viability of 6-ETI-sensitive cell line but does not decrease the viability of 6-ETI-resistant cell line.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Example 1: Materials and Methods

Electrophoretic Mobility Shift Assays

BC3 or LCL9001 cells were plated at $5*10^5$ cells/ml, and treated with the hit compounds at 25 μM or with NSC39368 at 5, 10, 25 and 50 μM for 24 hours. Nuclear extracts were obtained as previously described (Keller S. A. et al., *Blood.* 2000; 96(7):2537-42), and electrophoretic mobility shift assays (EMSAs) were performed using an NF-κB-specific oligonucleotide probe.

Viability Assays

Cell viability assays were performed by plating log-phase cells in RPMI complete media with 20% FBS at $1*10^5$ cells/mL, with concentrations of 6-ETI or phospho-6-ETI ranging from 0.1 nM to 100 μM. ATP content at 24, 48 and 72 hours post-treatment was measured by the CellTiter-Glo kit (Promega, Madison, WI), or by Trypan blue assay as indicated. The $LC_{50}$ for 6-ETI in each cell line was determined using online $EC_{50}$ software at changbioscience.com or using GraphPad Prism to determine the $LC_{50}$ for 6-ETI, phospho-6-ETI and nucleoside analogs in MM cell lines and primary MM patient samples.

Cell Cycle and Cell Death Assays

Assessment of cell death in cell lines and primary cells are described in the supplemental methods.

Immunoblotting

For all intracellular signaling studies, cell lines were plated at $2*10^5$ cells/mL or at indicated densities in RPMI-1640 with 20% FBS, and treated with the stated concentrations of 6-ETI, from 6 to 48 hours Immunoblotting was performed using the following antibodies: PARP (BD Pharmingen, 556494), LC3B (Cell Signaling, 2775S), phospho-Histone H2AX.X S139 (Cell Signaling, 2577S), GAPDH (Gene Tex, GTX100118), ADK (Santa Cruz, sc-365470) vFLIP 6/14 antibody was a gift from Mary Collins at University College of London, vCyclin (Abcam, ab12208), LANA (Advanced Biotechnologies, 13-210-100), β-Actin (Sigma A5316), p65 (Cell Signaling C22B4, p50 (Cell Signaling 3035), Oct-1 (Cell Signaling 4428), p-IκBα (Santa Cruz B-9 sc-8404), IκBα (Santa Cruz C-21 sc-371), pIKKα/β (ser 176)(Santa Cruz sc-21661), IKKα (Santa Cruz H-744 sc-7218).

Generation of 6-ETI-Resistant Cell Lines

To generate 6-ETI resistant clones, BC3 cells were plated in RPMI-1640 with 50 μg/mL Gentamicin and 20% FBS under 6-ETI selection in multiple 96-well plates at $1*10^5$ cells/mL. Selection was begun at 15 nM, 30 nM, or 60 nM 6-ETI. Cells were split every three days, with the dose of 6-ETI doubled at least 1×/week. Selection continued until a few clonal populations remained, after which the clones were expanded into fresh plates under selection with 10 μM 6-ETI. Clones retrieved were designated NSCE-1, NSCE-2, NSCE-3, NSCE-4, NSCE-5, NSCE-6, NSCE-7, NSCE-8, in chronological order of selection from the original plates. NSCE-4 and NSCE-5 ceased growth and were not included in the final analysis.

Additionally, in two mice in the low dose cohort of the xenograft trial (see below) tumors grow out beyond the 100-day trial cessation time point. The ascites from these mice were harvested ex vivo, and following Ficoll extraction, placed in culture in RPMI-1640 with 10% FBS. After 6-ETI viability assays determined these xenograft cell lines, designated 2-3low and 3-5low, to have decreased sensitivity to 6-ETI, they were placed under bulk selection in RPMI-1640 with 20% FBS and 10 μM 6-ETI to generate resistance. Re-testing determined the outgrowing cells to be completely resistant to 6-ETI ($LC_{50}$s>100 μM), and these were subsequently included in RNASeq analysis.

RNA Sequencing

RNA was extracted using the RNeasy mini kit (Qiagen). Illumina libraries were constructed from RNA with the Illumina Truseq Total RNA Library Preparation Kit (v2) and sequenced on Illumina HiSeq in single-end 51-bp mode. Raw data contained 50-64 million reads, or a total of 2,600-3,300 Gigabases, per sample. The methods used to analyze the RNA sequencing data are provided as supplemental methods. RNAseq data are available in the NCBI's BioProject database under accession number PRJNA362820.

RNA Sequencing Data Analysis

To search for single nucleotide variants (SNVs) and small indels in the human genome, raw data was mapped to human reference GRCh37 using Bowtie2 via Tophat2 v.2.0.11 (Cesarman E et al., *N Engl J Med.* 1995; 332(18):1186-91) and each tumor sample was compared against the two normal BC3 samples using Strelka v.1.0.10 (Sarek G. et al., *J Clin Invest.* 2007; 117(4):1019-28). Putative variants were annotated using snpEff v.3.3. Annotated variants were examined with a combination of custom shell scripts and manual visualization in Integrative Genomics Viewer (IGV) (Nayar U. et al., *Blood.* 2013; 122(16):2837-47) to identify candidates that were 1) present in tumor samples but in neither of the normal samples; 2) of a type that was likely to affect the protein (non-synonymous, start codon loss, stop codon gain, frame shift); and 3) recurrent in the tumor samples. Once candidates were identified, expression (or lack thereof) across each of the exons and introns of the candidate was checked with HTSeq-counts v.0.6.1 (Keller S. A. et al., *Blood.* 2006; 107(8):3295-302) and visualization in IGV. To search for variants in the KSHV genome, Bowtie2 was used to map the raw data to genomic reference NC_009333.1. SNVs and small indels in characterized viral domains were detected using a combination of Strelka v.1.0.10 and Samtools mpileup v.0.1.18 (Guasparri I. et al., *J Exp Med.* 2004; 199(7):993-1003), and annotated in snpEff v.4.0E using a database constructed around the Genbank record. No recurrent variants survived filtration for minimum read depth of 10 and a variant type likely to affect the structure of the protein. Samples were searched for differential expression using HTSeq-counts v.0.6.1 and applying EdgeR v.3.6.7 (Liu L. et al, *J Biol Chem.* 2002; 277(16):13745-51) using the exact negative binomial test on gene counts normalized by the trimmed mean of M-values (TMM) method of tumor samples compared to BC3 normal samples. Gene expression data from RNA sequencing was analyzed using Ingenuity Pathway Analysis software (Ingenuity Systems, Redwood, CA).

Computational Approach to 3D Modeling of Adenosine Kinase WT and Mutant Proteins (G239E and G243K)

The X-ray crystallographic structure of human adenosine kinase (ADK) (1BX4) was used as the initial structure with two adenosine molecules, one bound to its substrate binding site and the other to its ATP binding site (Yamamoto K. et al., *Acta Virol.* 1988; 32(5):386-92). To prepare the wild-type enzyme model, Schrödinger's Protein Preparation Wizard (Sastry G M et al., *Journal of computer-aided molecular design.* 2013; 27(3):221-34) was used for the addition of missing residues and atoms, removal of the adenosine molecule in the ATP binding site, removal of bad contacts, optimization of bond lengths and removal of all ions and water molecules. The structure was further optimized by the addition of hydrogen atoms using Schrödinger's Maestro interface. The prepared model was then used to generate two mutant structures, G239E and G243K, using Maestro. The adenosine molecule in the substrate-binding site was modified using Maestro to resemble 6-ETI. Six models of ADK were prepared to illustrate the positioning of the mutated residues with respect to either the bound adenosine or 6-ETI molecules.

In Vitro Kinase Assay

The ADK kinase assay kit was purchased from Novocib, France. ADK and ATP provided in the kit were premixed into provided kinase assay buffer. The reaction at 37° C. was started by addition of 6-ETI in DMSO at T=0, followed by quenching of 10 μL of the reaction by 30 μL acetonitrile in an eppendorf tube at 5, 10, 15, 30, 60, 120, 150, 180, and 360 minutes. The quenched reaction was briefly vortexed and centrifuged at ~7000 g, following which the supernatant was transferred into a fresh tube and stored at 4° C. for HPLC/MS analysis. A control reaction was set up containing ADK, ATP, and Inosine, in order to generate a standard peak for IMP, while ADK, DTT, and ATP controls were generated by dissolving individual kit components in a 3:1 acetonitrile: $dH_2O$ solution.

HPLC/MS Analysis for 6-ETI phosphorylation by ADK

LCMS separations were performed using a Waters ACQUITY UPLC system equipped with ACQUITY PDA (diode array), Waters Micromass SQD 2000 spectrometer, and a Waters ACQUITY BEH C18 column (1.7 μm, 2.1×100 mm). The solvent system consisted of 0.1% Formic Acid in Water (Solvent A) and 0.1% Formic Acid in Acetonitrile (Solvent B). Flow was set to 0.3 mL/min, and a gradient of 5-95% Solvent B was applied over a period of 3 minutes. Total runtime was 4 minutes. Eluents were detected using a PDA at a wavelength of 254 nm. Mass data was obtained in both positive and negative electrospray mode, at a cone voltage of 30V.

In Vivo Xenograft Models

The BC3 in vivo xenograft model was set up as previously described (6). Essentially, ~4-6 week old male NOD-SCID mice (Jackson Labs Stock #001303) were injected intraperitoneally (I.P.) with $1*10^7$ BC3NFRen-luc #3 cells and followed by in vivo imaging every three days. After imaging on day 5 to confirm establishment of the tumor, the mice were randomized to vehicle, low dose and high dose cohorts, with average tumor burden distributed evenly across the groups. Each dose cohort contained 10 mice. Mice were treated for nine days beginning at randomization with vehicle (PBS-Tween80), low dose 6-ETI (150 mg/kg/day), or high dose 6-ETI (300 mg/kg/day). Mice were treated with 200 mg/kg of the 6-ETI analogs (phospho-6ETI and 6-ETI cAMP) for 9 days. We monitored mice for tumor growth by live imaging and weighing, with sacrifice point determined to be a net gain or loss of 10% body weight over a week. Upon reappearance of refractory tumors, mice were retreated for a further 9-day interval, and followed for a total of 100 days. Compound effects were assessed on overall survival, progression-free survival and tumor burden by Kaplan-Meier curves generated using GraphPad Prism software, and determined p values by 2-tailed analysis with log-rank tests.

For the disseminated multiple myeloma xenograft model, CAG cells were kindly provided by Dr. Malcolm Moore lab at MSKCC. $1\times10^7$ of CAG cells stably expressing the HSV-TK-eGFP-luciferase fusion protein were injected intravenously into NOD/SCID (NOD/LTSZPrko/J, the Jackson Laboratory Stock #001303). Eight days after tumor induction, mice were randomized into control and treated cohorts and treated intraperitoneally with either PBS 0.05% tween 80 (vehicle) or 200 mg/kg of 6-ETI daily for 9 days. Tumor mass or bioluminescence (photons/s/$cm^2$/steradian) was evaluated by imaging the mice using IVIS Imaging system. Statistical analysis was done using a two-tailed, unpaired Student's t-test using GraphPad prism.

Statistical Analysis. In all cases in which two groups were compared, unpaired two-tailed Student's t-tests or log-rank tests were used to determine significance. A p-value <0.05 was considered statistically significant. All bar and line graphs show mean±SEM of three experiments.

Cell Lines and Culture Conditions

KSHV+ primary effusion lymphoma (PEL) cell lines (BC1, BC2, BC3, BC5, BCBL1, BCP1), EBV+ lymphoblastoid cell line LCL9001, EBV+ diffuse large B-cell lymphomas (DLBCL) with immunoblastic features (IBL1, IBL4), and EBV+ effusion DLBCL BCKN1 were cultured in RPMI-1640 medium (Invitrogen) supplemented with 50 μg/mL Gentamicin (Sigma-Aldrich) and 10% or 20% heat-inactivated fetal bovine serum, respectively. Uninfected DLBCL cell lines (Ly2, Ly7) were cultured in IMDM (Invitrogen) supplemented with 50 μg/mL Gentamicin and 10% FBS. Multiple myeloma (MM) cell lines U266 and MM1S were cultured in RPMI supplemented with 15% FBS and 50 μg/mL Gentamicin, while JJN3 was cultured in 40% IMDM/40% DMEM plus 20% FBS supplemented with 50 μg/mL Gentamicin. Hodgkin's lymphoma (L428, L1236) and Burkitt's lymphoma cell lines (BJAB, Namalwa) were maintained in RPMI-1640 supplemented with Gentamicin and 10% FBS. All of the PEL cell lines and IBL1 were established in our laboratory from lymphomatous effusions except BCBL1,which was obtained from the AIDS and Cancer Specimen Bank. Burkitt lymphoma cell lines Namalwa and BJAB as well as the multiple myeloma cell line U266 were obtained from the American Type Culture Collection (ATCC). JJN3 cell line and Hodgkin cell lines (L428, L1236) were obtained from DSMZ. DLBCL cell lines LY2 and LY7 were provided by Riccardo Dalla-Favera (Columbia University). MM1S cell line was provided by Dr. Giorgio Inghirami lab at Weill Cornell Medicine. Human CAG MM cell line stably expressing the HSV-TK-eGFPluciferase fusion protein was kindly provided by Malcolm Moore (Memorial Sloan-Kettering Cancer Institute) and was cultured in RPMI+20% FBS. All cell lines were maintained in a humidified incubator at 37° C. and 5% $CO_2$.

The xenograft cell line BC3NFκB-luc #6 was generated as previously described (Chang Y. et al., *Science.* 1994; 266(5192):1865-9). The double reporter cell line BC3NFRen-luc #3 was generated by transduction of this cell line using a lentiviral construct expressing renilla luciferase controlled by a constitutive promoter (retroviral LTR). These cells were maintained in RPMI-1640 supplemented with 15% FBS and 50 μg/mL Gentamicin, as well as 1.2 mg/mL Geneticin (Life Technologies) to maintain clonal selection.

Bone marrow specimens were obtained from multiple myeloma patients at the New York-Presbyterian Hospital under informed consent as part of an Institutional Review Board-approved study in accordance with the Declaration of Helsinki. Primary $CD138^+$ human myeloma cells were isolated by Ficoll-Hypaque density gradient centrifugation. The $CD138^+$ bone marrow myeloma cells were then enriched from this fraction to >95% purity using an automated MACS CD138 MicroBeads system (Miltenyi Biotechnology, Inc., Auburn, CA). Coculturing $CD138^+$ cells with HS5 stromal cells did not alter their sensitivity to 6-ETI treatment for short treatment course. PBLs were harvested from normal blood using Ficoll-Paque (Sigma-Aldrich) as described previously. Cells were plated in RPMI-1640 supplemented with 20% FBS.

Pancreatic adenocarcinoma PA-Tu-8988T cell line was kindly provided by Lewis Cantley's lab (Weill Cornell Medicine). Knock out of ADK in this cell line was achieved by transducing these cells with ADK shRNA Lentiviral Particles (Santa cruz) and selecting the stable cell line using 2 μg/ml Puromycin.

Cell Cycle Assays

BC3 cells in the exponential phase were seeded at a cell density of $2*10^5$ cells/mL. Cells were treated with 0.1% DMSO or with 6-ETI at a final concentration of 1 μM 6-ETI for 24 hrs for cell cycle. Post-treatment, cells were harvested, fixed and stained in Propidium Iodide (Roche). Subsequently, stained cells were analyzed by flow cytometry using BD FACS Aria II SORP cell sorter, and phases of the cell cycle modeled using FlowJo v7.6.5.

Apoptosis Assays

BC3 and IBL1 cells in the exponential phase were seeded at a cell density of 0.2 million cells/ml. Cells were treated with 0.1% DMSO or with 6-ETI at a final concentration of 500 nM or 5 μM for 24, 48 or 72 hrs. Post-treatment, cells were harvested and stained with 2.5 μL of Alexa Fluor 647 Annexin V conjugate (Life technologies) and 2.5 μL of 7-AAD (BD biosciences) and incubated for 15 minutes in the dark at room temperature. Subsequently, 200 μL of Annexin V binding buffer (BD Biosciences) was added to the cell suspension and cells analyzed by flow cytometry using BD biosciences LSRII machine.

Toxicity on Normal Primary Tonsillar Lymphocytes

Primary human tonsil specimens were obtained from the Weill Cornell/New York Presbyterian Institutional Biobank. Lymphocytes were isolated from human tonsil tissue by dissection and maceration in RPMI media. Lymphocyte-containing media was passed through a 70 μm filter and pelleted at 400 g for 7 minutes. RBC were lysed for 5 minutes in RBC lysing solution (0.15M ammonium chloride, 10 mM potassium bicarbonate, 0.1M EDTA). After dilution to 50 ml with RPMI, lymphocytes were filtered through a 0.4 μm filter, counted and pelleted a second time. Total B cells were isolated using magnetic cell sorting according to manufacturer instructions (Miltenyi Cat #130-091-151). Cells were plated at 2 million cells/ml in RPMI with 20% FBS and 100 μg/ml Primocin (Invivogen) and laid over gamma-irradiated CDW32 feeder cells. Cells were then treated with DMSO, 1 μM or 10 μM 6-ETI for 24 hrs. For the multi-color flow cytometry immunophenotyping, cells were pelleted and resuspended in FACS Wash buffer (PBS+0.5% FBS+0.1% Sodium Azide) containing B cell phenotype panel as follows for 15 minutes on ice: CD19-PE (16 μl), CD38-PECy7 (6 μl, BD Cat #560667), IgD-PerCP Cy5.5 (5 μl, BD Cat #561315), CD138-APC (5 μl, BD Cat #347207), CD27-APC H7 (5 μl BD Cat #560222). Volumes indicated were based on titrating the individual antibodies on primary tonsil lymphocyte specimens. After incubation, 100 μl FACS Wash was added and pelleted lymphocytes were washed with a further 200 μl of FACS Wash prior to being resuspended in 200 μl FACS Wash for analysis. Data was acquired on a BD LSR2 Flow Cytometer and analyzed using FlowJo software. The frequency of plasma cells was assessed based on singlet-gated cells expressing CD138.

6-ETI Effects on DNA Synthesis Using EdU Click-IT Assay

BC3 and U266 cells were seeded at a density of 0.5 million cells/ml and treated with DMSO only, 1 μM or 10 μM 6-ETI for BC3 cells and 5 μM 6-ETI for U266 cells for 24 hrs. At 24 hrs post 6-ETI treatment, 0.5 million cells of each of the treated conditions were labeled with 10 μM of EdU for 2 hours then fixed for 30 min using 2% paraformaldehyde supplemented with 0.3M sucrose. Cells were then washed in PBS and permeabilized with 0.2% saponin, PBS with 1% BSA and 0.3M sucrose for 20 min at room temperature. During this incubation time, a click-iT cocktail mix containing click iT reaction buffer, $CuSO_4$, alexafluor488 and click iT reaction buffer additive was prepared according to the manufacturer's instructions. Cells were washed in PBS after permeabilization and the click-iT cocktail mix was added for 30 min at room temperature in the absence of light. To visualize DNA, cells were counterstained with Hoechst (1:1000) for another 30 min then washed and resuspended in PBS with 1% BSA. 20 μl of the resuspended cells were combined with 20 μl of mounting media Fluoromount-G (Southern biotech) and cells were mounted on Ibidi μ-slides. Cells were imaged using DeltaVision image restoration microscope (Rockefeller center).

Immunofluorescence Staining, Image Acquisition and Analysis $1*10^5$ treated cells were pelleted into a 96-well round bottom plate. Cells were washed once with PBS, and fixed in PBS+2% paraformaldehyde+0.03M sucrose for 15 min at room temperature. Cells were then washed twice with PBS+1% BSA+0.03M sucrose, permeabilized with PBS+0.2% saponin+1% BSA+0.03M sucrose (IFA Wash) for 15 min at room temperature, and blocked for 1 hour in PBS+5% normal goat serum. Cells were then stained in IFA Wash containing phospho-histone-H2A.X (ser139) antibody (γH2AX) at 1:100 dilution overnight at 4° C. Following two washes with PBS+1% BSA+0.03M sucrose, cells were re-permeabilized and re-blocked as above prior to incubation for 1 hour at room temperature with anti-rabbit-AlexaFluor594+Hoechst diluted 1:1000 in IFA Wash. Cells were then washed twice with PBS+1% BSA+0.03M sucrose, resuspended in 30 μl Fluoromount-G (Southern Biotech) and transferred to 16-well Ibidi μ-slides for imaging. Images were taken on an Applied Precision Deltavision Image Restoration Microscope using Softworx analysis software. Z-stacks with a 0.2 μm step size were taken at 100× magnification. Stacks were subjected to deconvolution analysis and projections were made superimposing 5 representative z-planes to generate the final image.

6-ETI Synthesis

A mixture of ethanethiol (26 g, 419 mmol), methanol (16 ml), and sodium hydroxide (6.7 ml, 20% aqueous solution) was cooled to 0° C., using an ice water bath. The mixture was stirred for 30 minutes, at which point 6-chloropurine riboside (2 g, 7 mmol) was added. The resulting solution was slowly warmed to ambient temperature and stirred for 12 hours, then was neutralized with glacial acetic acid (2.4 ml). Solvent was then removed using rotary evaporator; a small amount of bleach was placed in the solvent trap to quench any remaining ethanethiol. The resulting crude product was dissolved in acetone (100 mL) and then passed through a short Celite plug to remove minor impurities. Concentration in vacuo provided 6-ETI as a white powder (2.11 g, 6.7 mmol, 96%). $^1$H NMR (500 MHz, $CD_3OD$) δ 8.69 (s, 1H), 8.59 (s, 1H), 6.09 (d, J=5.8 Hz, 1H), 4.75 (dd, J=5.5, 5.4 Hz, 1H), 4.37 (dd, J=5.1, 3.3 Hz, 1H), 4.18 (dd, J=6.2, 3.1 Hz, 1H), 3.91 (dd, J=12.4, 2.9 Hz, 1H), 3.78 (dd, J=12.4, 3.1 Hz, 1H), 3.42 (q, J=7.4 Hz, 2H), 1.45 (t, J=7.4 Hz, 3H).

Microplate-Based NF-κB Inhibition Assay

Exponentially growing BC3-derived reporter cell lines (BC3NFκB-luc #6 or BC3NFRen-luc #3), and unrelated luciferase expressing U251-pGL3 cells were resuspended in respective RPMI-1640 complete media, and plated in a 96-well tissue culture microplate at $7.5*10^5$ cells/mL and $3*10^5$ cells/mL, respectively, in the presence or absence of varying concentrations of test compounds. After 24 hours of incubation, the luciferase activity was measured using Steady-Glo Luciferase Assay System or Dual-Glo Luciferase assay system (Promega, Madison, WI), according to the manufacturer's instructions.

Lytic Reactivation qRT-PCR and Flow

BC3 cells in the exponential phase were plated at $2*10^5$ cells/mL, and treated with 100 nM, 1 μM, or 10 μM 6-ETI for 6, 24, or 48 hours. Expression of viral latent and lytic genes was determined using qRT-PCR as previously described (Soulier J. et al., *Blood.* 1995; 86(4):1276-80).

Lytic reactivation low was performed as previously described (Soulier J. et al., *Blood.* 1995; 86(4):1276-80). JSC1 B3.1 cells in the exponential phase were seeded at $2*10^5$ cells/mL and treated with 1 or 10 μM 6-ETI for 24 or 48 hours, or 20 ng/mL lytic inducer TPA for 48 hours.

In Vivo Xenograft Model of EBV-Associated Immunoblastic Lymphoma

The in vivo xenograft model of EBV-associated immunoblastic lymphoma was generated by injecting NOD-SCID mice (obtained from Jackson Laboratory Stock #001303) subcutaneously on the flank region with $5*10^6$ IBL-1 cells in 200 μl of 50:50 matrigel/cell suspension per mouse. After forming palpable or measurable tumors, mice were randomly grouped (n=3 per group) and treated intraperitoneally with vehicle PBS-Tween80 or 6-ETI (300 mg/kg/day) for 5 treatments over the course of 10 days where drug was administered three times a week. Tumor size was assessed by caliper measurement three times a week, and tumor volume (V) was calculated using the formula V=(length'Width^2)/2 where L=length or largest tumor diameter and W=width or the perpendicular tumor diameter. Relative tumor volume was determined according to the formula Vd/V0 where Vd is tumor volume on the day of measurement, and V0 represents the tumor volume on day 0 when the treatment started. At the end of the treatment course, two of the control mice were treated with vehicle PBS-Tween80 or 6-ETI (300 mg/kg) for 24 hr after which the tumors were harvested, fixed in 10% formalin and embedded in paraffin for histological examination and immunohistochemistry.

Ethics Statement

These studies were approved by the Weill Cornell Medical College Institutional Animal Care and Use Committee (IACUC).

Immunohistochemistry

Cases were collected from New York Presbyterian Hospital—Weill Cornell, and obtained with the approval and according to guidelines of the institutional review board. Primary cases used for immunohistochemistry included two primary effusion lymphomas, one extracavitary primary effusion lymphoma, two multiple myelomas, and two plasmablastic lymphomas Immunohistochemical staining of ADK (Polyclonal Rabbit antibody, dilution 1:25, Sigma) was accomplished using the Bond III Autostainer (Leica Microsystems, Illinois, USA). Formalin fixed and paraffin-embedded tissue sections were first baked and deparaffinized. Antigen retrieval was then followed by heating the slides in Bond Epitope Retrieval Solution 1(ER1) (Leica Microsystems) at 99-100° C. for 30 minutes. Sections were then incubated sequentially with the primary antibody, post-primary (equivalent to secondary antibody), polymer (equivalent to tertiary antibody), endogenous peroxidase block, diaminobenzidine (DAB) and hematoxylin for 15, 8, 8, 5, 10 and 5 minutes (Bond Polymer Refine Detection; Leica Microsystems), respectively. Finally the sections were dehydrated in 100% ethanol, and mounted in Cytoseal™ XYL (Richard-Allan Scientific, Kalamazoo, MI) Immunohistochemical staining of Cleaved Caspase 3 (Polyclonal Rabbit antibody, dilution 1:300, Cell Signaling) was accomplished as above, and used to assess apoptosis in vivo in mice with IBL1 xenografts treated with 6-ETI.

Example 2: Development of a High Throughput-Screening Assay Using a PEL-Specific NF-κB Reporter Cell Line The PEL cell line BC3 was previously modified through transduction of NFκB-firefly luciferase plasmid, followed by selection and subcloning, to yield the BC3NFκB-luc #6 single reporter cell line (Keller S A et al, *Blood.* 2006; 107(8):3295-302). The NIH Training Set (230 compounds) was screened using the BC3NFκB-luc #6 single reporter cell line, and optimal assay conditions for high-throughput screening (HTS) were determined. The established cell-based luciferase reporter assay was used to screen the NIH Diversity Set (1981 compounds) at 5 μM, yielding 60 primary hits that demonstrated at least 50% NFκB-luciferase inhibition, for an initial hit rate of 3%. Re-testing of these hit compounds determined 50 to be genuine.

As a next step to determine specificity, the inventors developed a secondary assay, wherein the single reporter cell line was lentivirally transduced with a constitutive renilla luciferase construct. The transduced cell line was sub-cloned to generate the double reporter cell line BC3NFRen-luc-#3. 50 hit compounds were tested using the double reporter cell line, as well as an additional control cell line U251-pGL3, derived from a glioma cell line U251, which expresses firefly luciferase constitutively under the control of the SV40 promoter (kindly provided by G. Mellilo, National Cancer Institute). Screening the double reporter and control cell line led to the identification of three hit compounds that were found to possess specific anti-NF-κB activity against PEL cells. Detailed chemoinformatic analysis was performed on these hit compounds and identified 66 additional analogs in the NIH compound repository, which were screened by the double reporter assay for structure activity relationship (SAR). Results from this analysis informed further analog identification; 39 additional analogs were screened by the double reporter assay in this second-tier analysis. Re-screening validated three analogs of two of the parent compounds as additional hits for NF-κB inhibition in PEL cells.

Example 3: Selection of 6-ETI

The inventors examined the six hit compounds obtained at the end of HTS for inhibition of the NF-κB pathway in parental BC3 cells. The compound NSC39368 effectively inhibited active heterodimer p65/p50 binding to the NF-κB response element by electrophoretic mobility shift assay (EMSA). This inhibition occurred in the BC3 PEL cell line, but not in a control lymphoblastoid cell line (LCL9001) containing EBV. This result identified NSC39368 or 6-ethylthioinosine, a nucleoside analog, hereafter referred to as 6-ETI, as the most promising compound for further investigation.

NF-κB reporter assays performed on BC3NFRen-luc #3 cells confirmed that 6-ETI inhibited NF-κB activity in this cell line as early as 6 hours post-treatment. 6-ETI treatment in BC3 cells was found to decrease levels of active subunit p65 in the nucleus, while leaving inactive subunit p50 unchanged, and it also decreased levels of IL6, an NF-κB dependent gene in PEL cells. Other components of classical NF-κB signaling, including IKKα, IKKβ, and IκBα were not consistently affected by 6-ETI treatment. Thus, like other inhibitors of NF-κB (Guzman J R. et al., *Scientific reports.* 2013; 3(1629); Perez M. et al., *Chem Biol Interact.* 2014; 214(69-76)), 6-ETI inhibited p65 nuclear accumulation, but the mechanism for this selective inhibition of p65 nuclear localization in PEL was not evident from immunoblot analysis of known upstream regulators of this process.

Example 4: 6-ETI Specifically Inhibits PEL Cell Viability

Figure 1C:
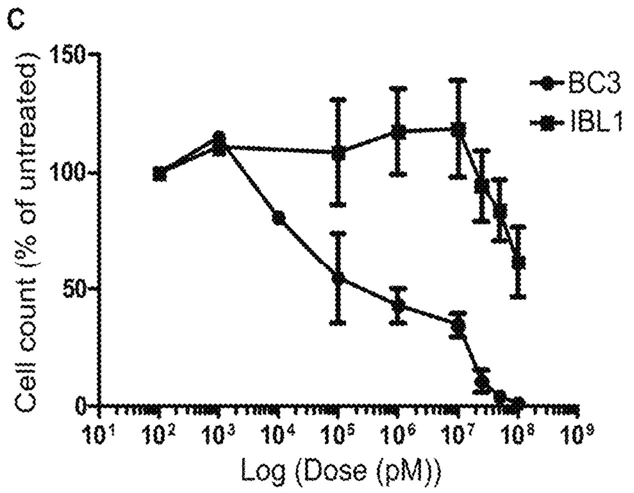
Figure 1D:
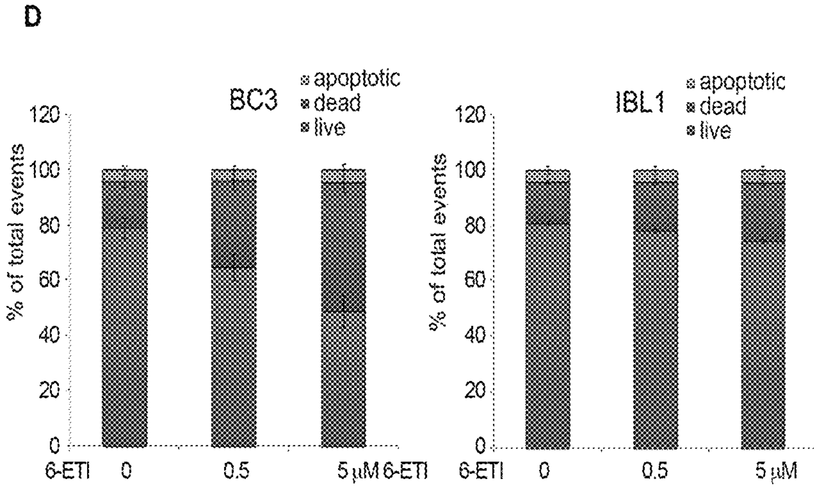

To assess toxicity and confirm selectivity towards PEL, 6-ETI was examined for its effectiveness against a panel of cell lines, including KSHV+ PEL, KSHV+/EBV+ PEL, EBV+ immunoblastic lymphomas (IBL), EBV+ lymphoblastoid cell lines (LCL), EBV− Hodgkin's lymphoma (HL) cell lines, EBV+ and EBV− Burkitt's lymphoma (BL) cell lines, virus-negative diffuse large B-cell lymphoma (DLBCL) cell lines, several of which are known to be NF-κB-dependent, and normal peripheral blood leukocytes (PBLs). An ATP-based luminescent cell viability assay (CellTiter-Glo) was used to determine $LC_{50}$s at 48 hours (FIG. 1B) after treatment initiation, and observed a striking correlation of effectiveness with KSHV− infection status of the cell. Cell lines that were KSHV+ had $LC_{50}$s in the mid-nM range, varying from ~30-435 nM, while all KSHV− cell lines tested, regardless of differentiation stage, tumor type, EBV infection status, or NF-κB dependence, exhibited $LC_{50}$s in the μM (10-80 μM) range, showing an average fold-difference in sensitivity of ~275× (p=0.0001, unpaired t-test). To ensure concordance between ATP levels and cell death, viability for a selected PEL and non-PEL cell line was also assessed by Trypan-blue exclusion, yielding $LC_{50}$s of 74 nM and 134 μM, respectively (FIG. 1C). 6-ETI treated PEL cell line also had a higher proportion of dead cells as determined by Annexin V/7-AAD staining (FIG. 1D). Notably, the 6-ETI doses that had been found to be effective in inhibiting NF-κB in PELs were in the range of 10-50 μM, while cell viability was impacted at nM doses, indicating that NF-κB inhibition was a secondary effect of this compound and not the primary mechanism involved in cell death.

Example 5: PEL Cells Undergo Apoptosis and Necrosis Upon 6-ETI Treatment

Figures 2A, 2B, 2C:
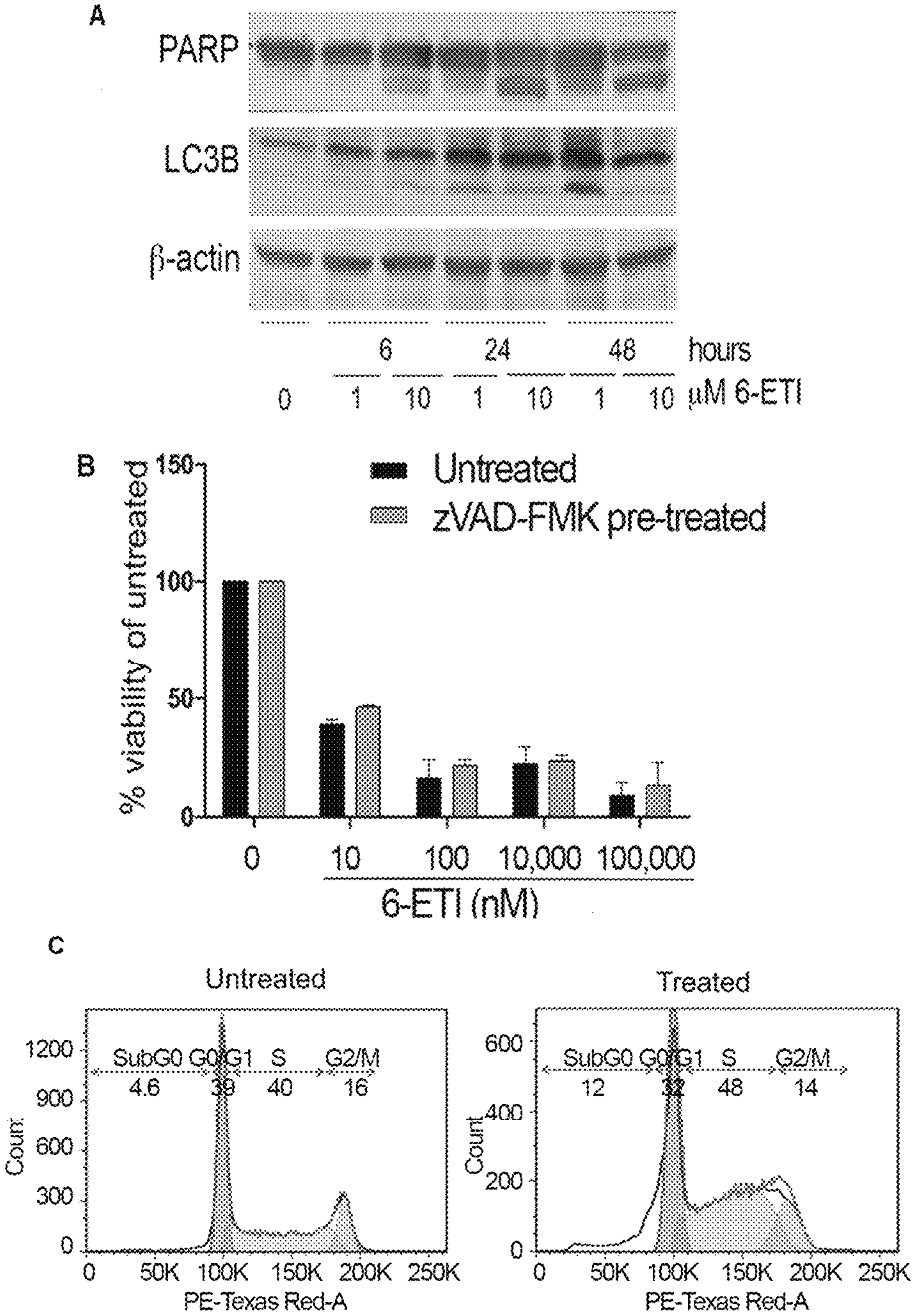
FIGS. 2A-2F. Mechanism of 6-ETI induced cell death. (A) BC3 cells treated with the indicated doses of 6-ETI at the shown time points were analyzed by Western blotting on whole cell extracts for PARP cleavage as an indicator of apoptotic induction and for LC3B cleavage as an indicator of autophagosome formation. Actin and GAPDH were used as loading controls, and results shown are representative of at least three independent experiments. (B) BC3 were pretreated or not with 80 μM zVAD-FMK, a pan-caspase inhibitor, to inhibit apoptosis. After 3 hours, cells were treated at the indicated doses of 6-ETI. Cells lysed at 48 hours were examined by CellTiter-Glo to measure viability, with results normalized to untreated cells at each condition. The mean±SEM of three independent experiments is shown. (C) BC3 cells treated with DMSO or 1 μM 6-ETI for 24 hours were stained with propidium iodide, followed by flow-based cell cycle analysis. The obtained histograms were modeled by FlowJo. Results shown are representative of at least three independent experiments. (D) BC3 cells were treated with DMSO, 1 μM or 10 μM 6-ETI for 24 hrs then labeled with 10 μM EdU for 2 hrs. EdU incorporation into the newly synthesized DNA was visualized by staining cells using click-iT EdU Alexa Fluor 488 cocktail and the nucleus was counterstained using Hoechst. Immunofluorescence images are representative of two independent experiments. (E) Immunoblotting for γH2AX is shown after treatment with 6-ETI at the indicated time points and doses. Result shown is representative of three independent experiments. (F) Representative immunofluorescence images of two independent experiments showing nuclear localization of γH2AX after treatment with 6-ETI for 48 hours. As a positive control, BC3 cells were treated with UV radiation to induce DNA damage.

In order to determine the mechanism of 6-ETI-induced cell death, the inventors examined treated cells for activation of classical cell death pathways, including apoptosis, autophagy, and necrosis. The inventors tested the effect of treatment of two PEL cell lines with 1 μM of 6-ETI, as this concentration is close to the $LC_{95}$, which allowed to capture the full effect of the drug while not having any effect in resistant cell lines. The inventors also tested 10 μM, which exceeds the effective concentration, but provides information on earlier effects and is a dose at which there is no toxicity or any other appreciable effects in resistant cell lines. PARP cleavage was used as a marker of apoptosis in PEL cells treated with 6-ETI. As seen in FIG. 2A, 6-ETI induced small but observable increases in apoptosis in BC1 and BC3 cells at the 1 μM dose as early as 24 hrs. Because KSHV vFLIP has also been implicated in autophagic cell death, Western blotting was performed to determine the extent of activation of this pathway after 6-ETI treatment in PEL cells. There was some induction of autophagy, as assessed by appearance of the LC3B cleavage product, apparent at the 1 μM dose at the 24 hr time point (FIG. 2A).

Cells with low ATP levels have been observed to preferentially undergo necrosis over apoptosis (McCall K., et al., *Curr Opin Cell Biol.* 2010; 22(6):882-8). Since 6-ETI treated cells have low ATP content upon treatment as determined by CellTiter-Glo assay, the inventors examined PEL cells for the appearance of necrosis, as determined by caspase-independent cell death. In order to do this, the inventors pre-treated PEL cells with the pan-caspase inhibitor zVAD-FMK, followed by 6-ETI treatment at selected doses (FIG. 2B). PEL cells pre-treated with zVAD-FMK still underwent cell death upon 6-ETI treatment compared to untreated cells. This confirmed that 6-ETI-induced cell death is largely caspase-independent, and that necrosis is a major pathway of cell death induced by this compound, although apoptosis and autophagy also occur, at least in a subset of cells and under some experimental conditions.

Example 6: 6-ETI Induces S-Phase Arrest

Figures 2D, 2E, 2F:
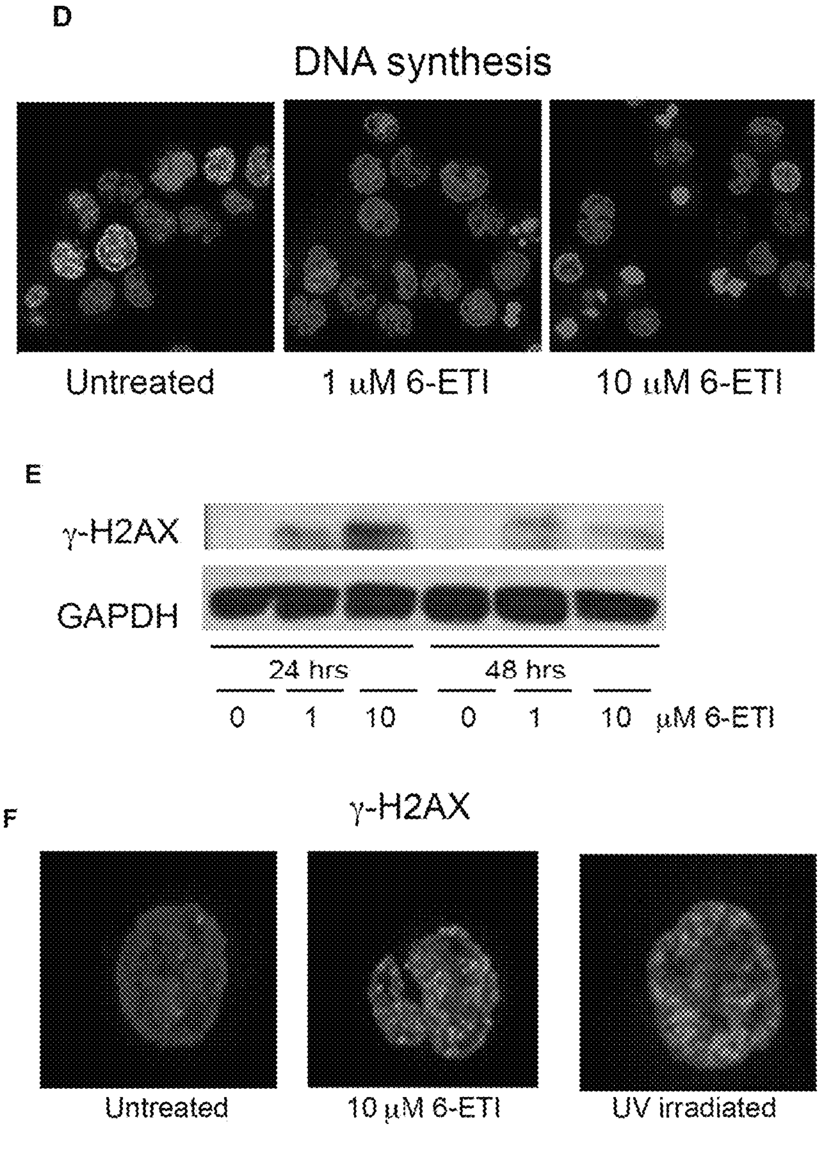

The effects of 6-ETI treatment on the cell cycle were examined by propidium iodide flow cytometry. The inventors observed an increase in the fraction of cells in the sub-G0 phase upon 6-ETI treatment likely reflective of both necrosis and apoptosis, but the inventors also detected a reproducible increase in the percentage of cells in S-phase 24 hours post-treatment in BC3 cells. This represents an induction of S-phase arrest by the compound, as modeled by FlowJo (FIG. 2C). This accumulation of cells in the S phase is consistent with incorporation of 6-ETI into DNA during DNA synthesis, thereby blocking extension and causing stalling of replication forks. The inventors investigated the effect of 6-ETI on DNA synthesis by using a Click-iT EdU assay, which showed a complete inhibition of DNA synthesis upon 1 μM treatment of 6-ETI for 24 hours (FIG. 2D). Similarly, a reduction in BrdU incorporation upon exposure to 6-ETI treatment was also observed. This process leads to the formation of double-stranded breaks (DSBs) in DNA, thus triggering a DNA damage response, a phenomenon that has been observed with other nucleoside analogues (Ewald B., *Oncogene.* 2008; 27(50):6522-37). To determine whether 6-ETI similarly triggers a DNA damage response, the inventors assessed 6-ETI treated PEL cells for the presence of γH2AX, a well-known marker of DSBs Immunoblot analysis showed the appearance of γH2AX at 24 hours post treatment with 1 μM and 10 μM dose of 6-ETI (FIG. 2E). Nuclear accumulation of γH2AX was also seen by immunofluorescence (FIG. 2F), confirming that 6-ETI induces DNA damage.

Example 7: 6-ETI Does Not Inhibit Viral Latent Protein Levels

Since several viral latent proteins have been shown to directly modify important cellular signaling pathways, such as vFLIP's critical role in sustained NF-κB induction in PELs (Guasparri I. et al., *J Exp Med.* 2004; 199(7):993-1003), and since 6-ETI was isolated using a PEL-specific NF-κB reporter assay, the inventors postulated that this compound may exert its effects on PEL cell viability and NF-κB signaling through inhibition of vFLIP or other oncogenic viral gene products. Accordingly, the inventors examined the levels of the major KSHV latent proteins upon 6-ETI treatment by immunoblotting. However, no reduction was seen in latent viral protein expression, as determined by western blot analysis of KSHV latent proteins LANA, vFLIP and vCyclin. This unexpected effect was also observed when treated cells were examined for levels of the transcripts of LANA, vIl-6, ORF50 and K8.1 genes by qRT-PCR at 24 hours.

Since lytic reactivation triggered by the compound could be a mechanism of cell death, the inventors examined 6-ETI's effects on viral lytic gene expression. Analysis of immediate-early (ORF50) and late lytic transcripts (K8.1) by qRT-PCR demonstrated a minor induction of immediate-early and mild suppression of late transcripts at the highest dose. The immediate-early gene vIL-6, which has also been found to be expressed at low levels during latency (Chandriani S. et al., *J Virol.* 2010; 84(11):5565-73), was increased in expression at higher doses, paralleling the other latent genes. To further investigate the compound effects on the lytic viral cycle, the inventors employed the recombinant KSHV (rKSHV.219) infected JSC1 PEL cell line, that expresses GFP under the control of the EF1-alpha promoter in all cells, and RFP under the control of the early lytic PAN promoter of KSHV (Vieira J. et al., *Virology.* 2004; 325(2):225-40). This cell line thus expresses GFP constitutively, and RFP only when the lytic cycle is activated. There was an induction of lytic reactivation by 6-ETI compared to the lytic phase inducer TPA in a small proportion of cells, which increased at higher doses and longer time points. This induction of lytic reactivation does not explain the cell death that occurs in a larger proportion of PEL cells with toxic doses of 6-ETI.

Example 8: 6-ETI is Highly Effective In Vivo

Figures 3A, 3B:
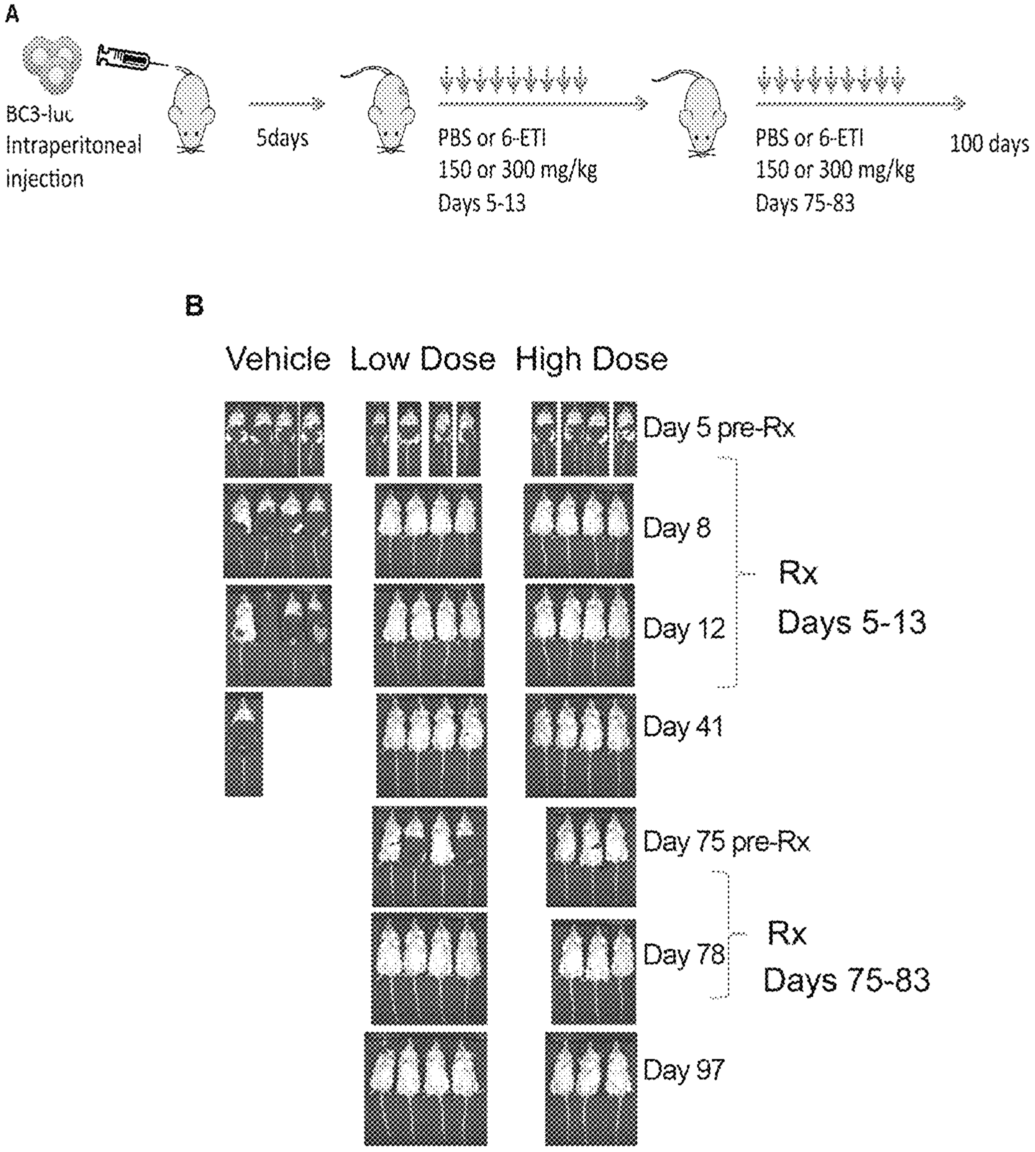
FIG. 3A. 6-ETI is effective in vivo in a PEL xenograft mouse model. (A) Scheme of BC3-luc tumor cell engraftment in NOD-SCID mice and treatment with 6-ETI. (B)
Figures 3C, 3D, 3E:
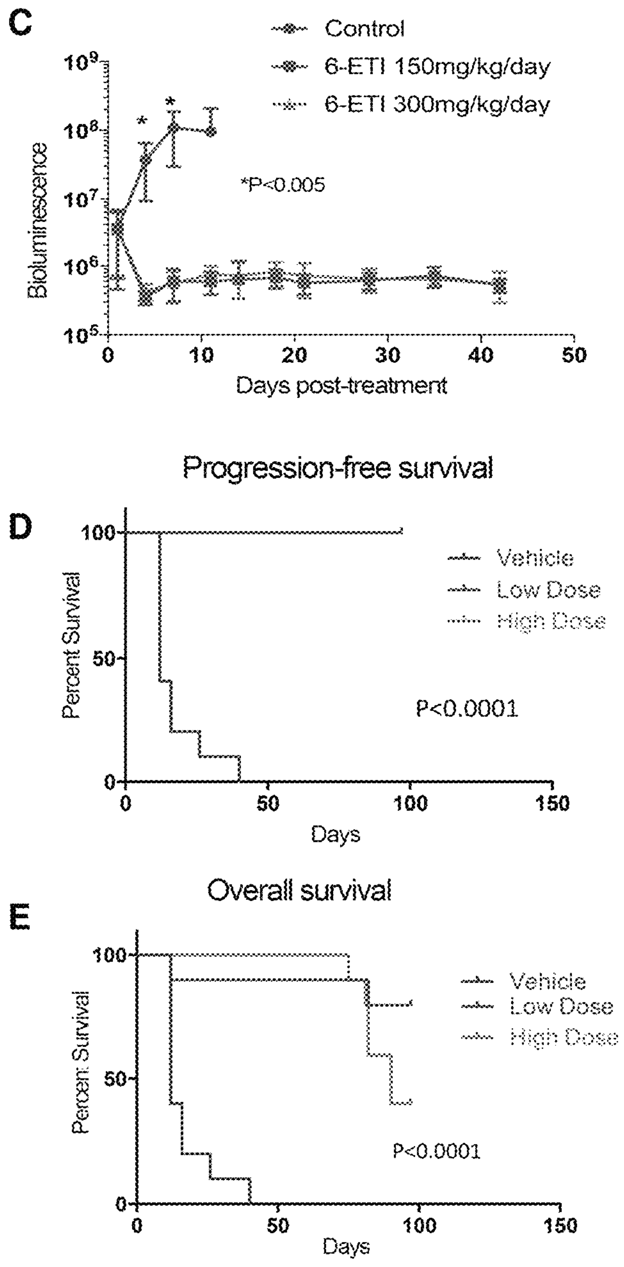

6-ETI was tested using a traceable reporter xenograft model of PEL (Keller SA. et al., *Blood.* 2006; 107(8):3295-302). Cohorts of 10 mice were treated with vehicle alone, 150 or 300 mg/kg/day for 9 days (FIG. 3A). These doses were selected based on NIH in vivo anticancer drug screens with this drug, which used 200 mg/kg for 9 days with no reported toxicities. Luciferase imaging in vivo clearly showed a striking and immediate regression of the implanted xenograft within three days of treatment, which began at day 5 post-engraftment (FIG. 3B). Quantification of the luminescent signal as a measure of tumor burden is shown in FIG. 3C. In two mice treated at the lower dose level (150 mg/kg/day), tumor recurred two months after cessation of treatment, but responded again upon re-treatment, documenting an impressive response in cases of both incipient and well-established tumors. Kaplan-Meier analysis of the trials indicated a startling protective effect of 6-ETI treatment on the length of progression-free survival in mice (FIG. 3D, p<0.0001), with the study being terminated at the 100-day mark. There were no obvious toxicities from the treatment, although a few long-surviving mice in the treatment groups succumbed to unrelated infections at the site of repeated luciferase injection. Nevertheless, both low dose and high dose treated mice had a significant prolonged overall survival compared to untreated mice as shown in FIG. 3E.

Example 9: Mechanism of Selectivity Revealed by Unbiased Genomic Analysis

In order to determine the primary target of 6-ETI at effective doses, unbiased genomic sequencing was performed on resistant clones obtained from the parental PEL cell line BC3 through selection. The inventors used transcriptome sequencing for this analysis, in order to simultaneously obtain gene sequences and expression levels. To produce resistant clones, BC3 cells were grown in 96-well plates at escalating doses of compound up to 10 μM over the course of several months, and the resultant clones were tested by viability assay for sensitivity to the compound. Six independent clones were obtained arising from different wells of two plates, NSCE-1, NSCE-2, NSCE-3, NSCE-6, NSCE-7, and NSCE-8, that were fully resistant to 6-ETI. Additionally, the inventors were able to culture ex vivo tumor cells from two mice in the low-dose cohort of the xenograft trial who developed late recurrent tumors after two rounds of treatment, and place these under selection with 6-ETI to yield completely resistant xenograft outgrowth clones. These cell lines were designated 2-3 low and 3-5 low.

RNA was extracted from resistant clones and duplicate samples of the parental cell line, and transcriptome sequencing followed by bioinformatic analysis (51 bp single-end reads, mean library size 58.5 million reads per clone) was performed to identify mutations linked to resistance. The inventors reasoned that recurrently observed mutations across multiple independent clones might provide key information regarding either the target of the compound or other pathways important for its mechanism of action. Both human and KSHV genomes were used as reference sequences for comparison, in order to enable comprehensive target identification. The only recurrently altered gene identified by single nucleotide variant (SNV) analysis of the RNA sequencing data was adenosine kinase (ADK). Two independent mutations (G239E and E243K) were identified in this gene in two unrelated resistant clones (FIG. 4A).

Example 10: 6-ETI Requires Endogenous ADK for Activity

ADK is the enzyme that catalyzes the transfer of gamma-phosphate from ATP to adenosine or inosine, in the process forming AMP and ADP. This reaction thus constitutes the first step of de novo purine biosynthesis, and makes ADK an essential enzyme whose knockout is lethal in mice (Boison D. et al., *Proc Natl Acad Sci USA.* 2002; 99(10):6985-90). ADK is required to control levels of cellular adenosine, which can be toxic if left unregulated (Newby A C. et al., *Biochem J.* 1985; 226(1):343-4), while ADK inhibition serves a host of other protective signaling functions (Berne R M., *Cardiovasc Res.* 1993; 27(1):2; Boison D., *Glia.* 2012; 60(8):1234-43).

The ADK mutations were modeled based on the X-ray crystallographic structure of human adenosine kinase (1BX4) using Schrödinger's Maestro (FIG. 4A). The inventors found that the mutated residues do not directly interact with the substrate or residues in the substrate binding site, but are close to it and therefore may conceivably contribute to the observed phenotype by affecting the conformational dynamics of the kinase. The inventors examined this gene in depth across all seven resistant clones, and found recurrent changes in the form of exon loss sparing the active site in three additional cases. In the two cases where there were no mutations or active site deletions, there was a significant (10-fold) downregulation of gene expression compared to the control cell lines. These results indicated that ADK inactivation confers PEL cell resistance to 6-ETI. Conversely, there were no recurrent missense or nonsense mutations in KSHV genes occurring within the resistant cell lines, or significant changes in viral gene expression. There was no over-expression of multi-drug efflux pumps either, although there were transcriptional changes in a number of genes.

The inactivation of ADK in every single resistant clone suggests two alternative scenarios: 1) that ADK is a direct target of 6-ETI and that ADK is necessary for the survival of PEL cells; or 2) that 6-ETI is a pro-drug that is activated by ADK. The latter possibility is supported by previous data indicating that ADK can activate other nucleoside analogs, including several important antiviral compounds such as ribavirin (Willis R C. et al., *Proc Natl Acad Sci USA.* 1978; 75(7):3042-4; Wu J Z et al., *Antimicrob Agents Chemother.* 2005; 49(6):2164-71; Mori K. et al., *Hepatology.* 2013; 58(4):1236-44), triciribine (Ptak R G. et al., *AIDS Res Hum Retroviruses.* 1998; 14(15):1315-22), mizoribine (Koyama H, and Tsuji M, *Biochem Pharmacol.* 1983; 32(23):3547-53), and tiazofurin (Saunders P P. et al., *Cancer Res.* 1990; 50(17):5269-74), although these compounds can also be activated by a variety of other kinases (Gallois-Montbrun S. et al., *Mol Pharmacol.* 2003; 63(3):538-46). Such a model was also supported by the locations of the observed mutations, one at and one near the active site of the enzyme, suggesting the involvement of such interactions in drug activity.

In order to differentiate between these two scenarios, BC3 cells were first treated with two different ADK inhibitors: A-134974 (McGaraughty S. et al, *J Pharmacol Exp Ther.* 2001; 296(2):501-9) and ABT-702 (Jarvis M F. et al., *J Pharmacol Exp Ther.* 2000; 295(3):1156-64). Neither of these inhibitors showed toxicity, with $LC_{50}$s in BC3 cells of >10 μM (FIG. 4B), in contrast to their known $IC_{50}$ of ADK inhibition in intact cells of 50 nM and 51 nM, respectively. To test the alternative model that ADK activates 6-ETI, 6-ETI viability assays were performed in PEL cells that were pretreated with these highly selective ADK inhibitors. It was demonstrated through competitive viability curves on BC3 cells, that pre-treatment with these inhibitors effectively rescued PEL cells from cell death induced by 6-ETI treatment (FIG. 4C).

The mechanism of activation of some nucleoside analogs by ADK involves phosphorylation at the 5' end of the 'prodrug', converting the molecule into the active 'drug' form (Wotring L L. et al., *Cancer treatment reports.* 1986; 70(4):491-7). The inventors examined if 6-ETI is similarly phosphorylated by ADK using an in vitro kinase assay in which ADK and ATP were mixed with 6-ETI and quenched by acetonitrile at different time points. Samples were injected into an HPLC, followed by MS analysis to enable identification of the putative phospho-6-ETI product. HPLC revealed the appearance of a second peak with a lower retention time (1.57 minutes) compared to the 6-ETI standard (1.76 minutes) as early as 5 minutes after the start of the reaction, and more apparent at 60 minutes. MS analysis of the 1.57 minute eluent from the 60 minute sample indicated this new peak contained a primary species of 391.3 Da. According to the [M-H] rule for negative electrospray mode of MS, this corresponds exactly to the expected molecular weight of activated phospho-6-ETI, thus conclusively proving that ADK phosphorylates 6-ETI directly.

Example 11: Endogenous ADK Levels Determine Sensitivity to 6-ETI

Figures 5A, 5B, 5C, 5D:
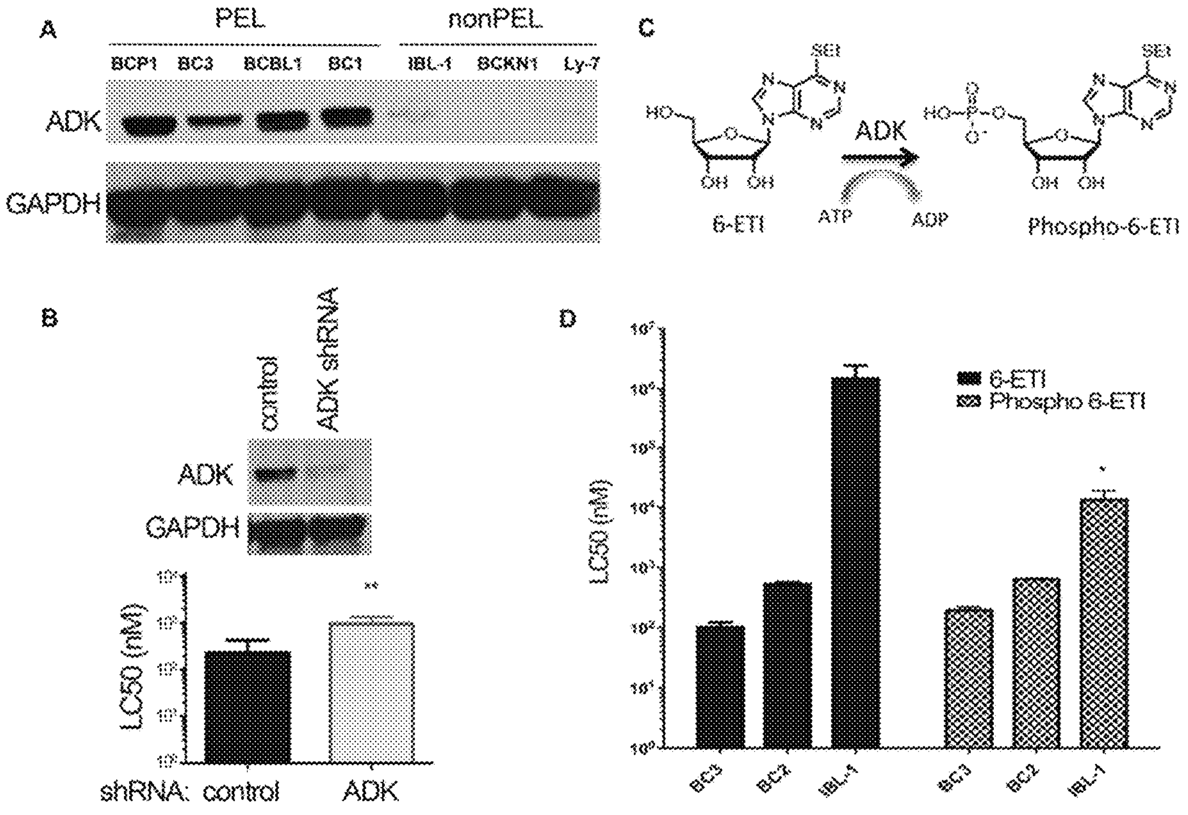

The inventors assessed whether expression of higher levels of ADK enabled enhanced processing of 6-ETI into its active phosphorylated form, which could explain the selectivity of 6-ETI to PEL cells. A panel of representative PELs and non-PELs were examined for ADK expression by immunoblot 24 hours after plating at cell densities used for the viability assays (FIG. 5A). Results clearly indicated that PEL cell lines express higher ADK levels than non-PEL, consistent with their heightened sensitivity to 6-ETI. To confirm that this endogenous ADK is necessary to confer sensitivity to 6-ETI, the inventors attempted to knock down ADK in PEL cell lines using lentiviral transduction but complete suppression was not achieved. Therefore, the inventors used a carcinoma cell line (PA-Tu-8988T) also with high ADK expression and which is more amenable to lentiviral transduction to test if genetic suppression of ADK affects sensitivity to 6-ETI. In this experiment, ADK knockdown resulted in a log increase in $LC_{50}$ (FIG. 5B). Thus, ADK activity appears to be a prerequisite for susceptibility to 6-ETI. To further test the model that ADK converts 6-ETI into its monophosphorytated active form (FIG. 5C), the inventors synthesized phospho-6-ETI and tested it in PEL and the resistant IBL-1 cell line. FIG. 5D shows that this modification partially overcomes resistance in IBL-1 cells that express low levels of ADK.

ADK levels were examined for three different resistant cell lines at higher plating densities, and it was found that there was a clear upregulation of ADK with crowding, although this was most robust for the IBL1 cell line, which is an EBV-infected immunoblastic lymphoma. If ADK expression levels were a major determinant of susceptibility to 6-ETI treatment, then sensitivity in non-PEL cell lines may be induced at plating conditions that increase their endogenous ADK levels. To test this hypothesis, IBL1, LY7 and BCKN1 cells were plated at a higher cell density ($5*10^5$ cells/mL), and viability assays were performed using 6-ETI dose response curves. The $LC_{50}$s under these alternate plating conditions decreased strikingly from those determined at the original assay conditions, showing that sensitivity in resistant lymphoma cell lines could be induced by altered cell densities. Taken together, these data show that there is a strong correlation between ADK levels and sensitivity to 6-ETI, explaining the selectivity of PEL cells for 6-ETI-induced toxicity.

The inventors further tested the idea that different experimental conditions, and specifically in vivo growth of some tumor cells as would occur in naturally occurring malignancies, is associated with high ADK expression, which could predict response to 6-ETI treatment. The inventors examined whether the immunoblastic lymphoma cell line IBL1 expresses ADK in vivo using a mouse xenograft model and assessed tumor responses following treatment with 6-ETI. The inventors found that this compound reduced the rate of tumor growth in mice, although responses were not as dramatic as those seen in PEL. Ex vivo tumors from these mice demonstrated expression of ADK in a proportion of tumor cells, as evaluated by immunohistochemistry, as well as some apoptosis induced by treatment in vivo, as determined by increased cleaved caspase 3 positivity. Thus, expression of ADK in vivo is associated with partial tumor responses to 6-ETI in an EBV+ immunoblastic lymphoma cell line.

Figure 6A:
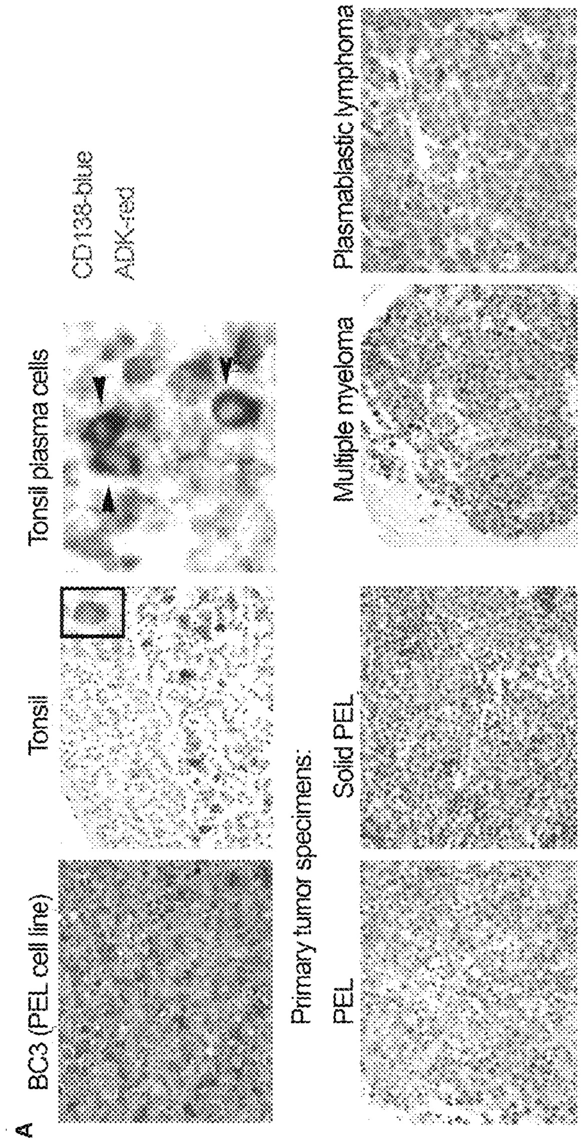
Figures 6B, 6C, 6D, 6E:
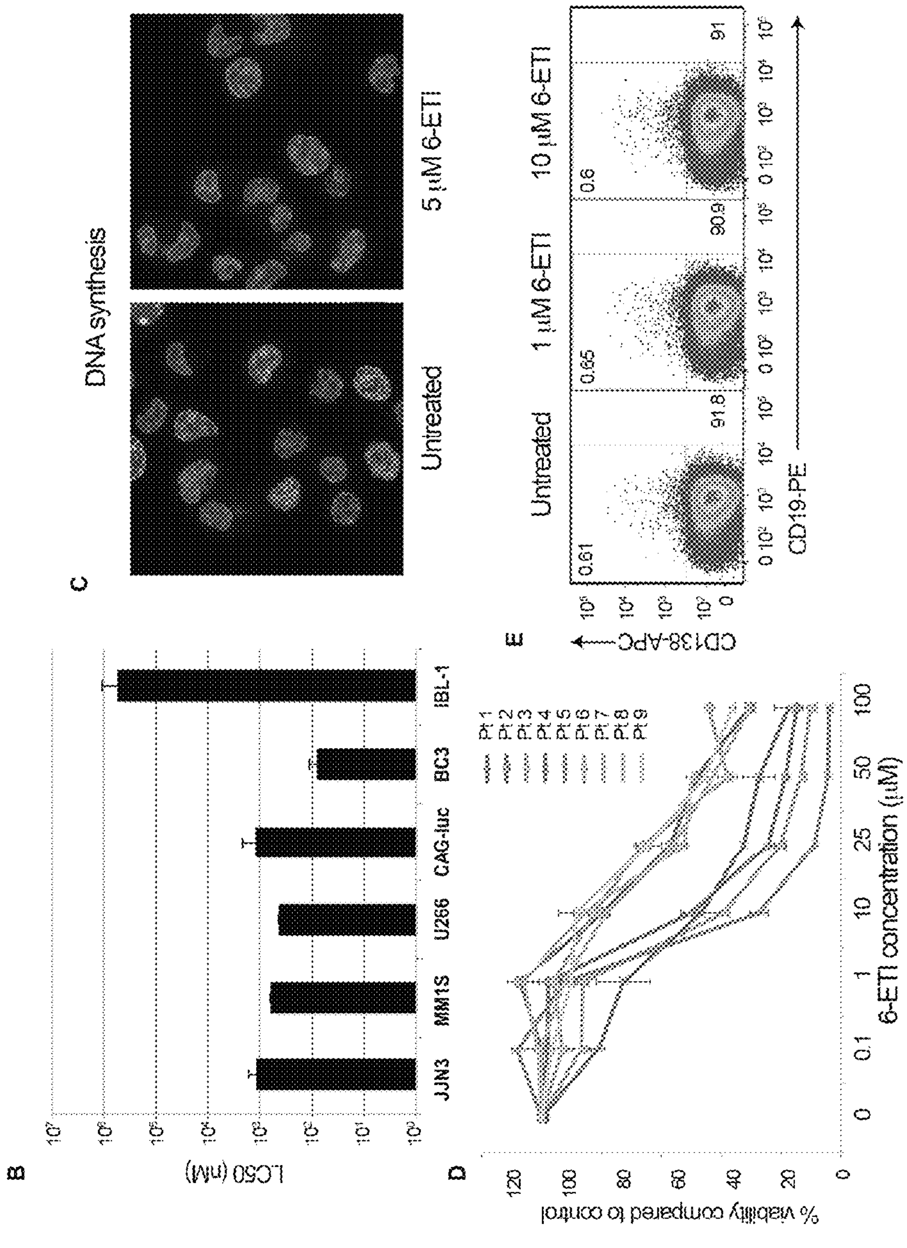

Example 12: ADK Expression May be Used as a Biomarker for Sensitivity to 6-ETI The clear correlation between 6-ETI sensitivity and ADK expression strongly suggested that other malignancies that express ADK may be sensitive to this drug. However, there is little information regarding ADK expression in lymphoid tissues and lymphoid malignancies, and cancer in general, in vivo. The inventors therefore performed immunohistochemistry for ADK in human tonsils, and found that normal plasma cells are positive, based on morphology and co-staining with CD138 (FIG. 6A). The inventors also confirmed expression of ADK in primary biopsy samples of PEL and extra-cavitary PEL. Given that PEL most closely resembles plasma cells immunophenotypically (CD138+) and by gene expression profiling (Gaidano G. et al., *Blood.* 1997; 90(12):4894-900; Klein U. et al., *Blood.* 2003; 101 (10):4115-21; Jenner R G. et al., *Proc Natl Acad Sci USA.* 2003; 100(18):10399-404), the inventors hypothesized that ADK is highly expressed in other malignancies of plasma cell origin, namely multiple myeloma (MM) and plasmablastic lymphoma (PBL). All four cases of MM and both cases of PBL evaluated showed clear expression of ADK (FIG. 6A). The inventors therefore evaluated four MM cell lines, JJN3, MM1S, U266 and CAG for their sensitivity to 6-ETI treatment. As was the case for PEL, MM cell lines were sensitive to inhibition by 6-ETI and phospho-6-ETI, with $LC_{50}$s in the high nM range (FIG. 6B). Primary multiple myeloma samples cultured ex vivo also showed sensitivity to 6-ETI, indicating that this sensitivity is not exclusive to cell lines (FIG. 6D). Co-culture with bone marrow stromal cells during treatment was assessed for two different patient samples, in parallel with separated myeloma cells alone, and there was no significant difference in sensitivity. 6-ETI also suppressed DNA synthesis in MM cells (FIG. 6C), and cytotoxicity was associated with induction of apoptosis, autophagy and activation of a DNA damage response as indicated by western blot detection of LC3B cleavage, PARP and its cleaved form and phosphorylated H2AX (γ-H2AX).

Since 6-ETI needs to be phosphorylated by ADK to render it into the active drug, the inventors made the phosphorylated version, called p6-ETI, expecting to bypass ADK. While this drug was equally effective as 6-ETI in sensitive cell lines (expressing ADK at high levels), the inventors observed only partial sensitivity in some ADK-low resistant cell lines, but not in all of them. Thus the inventors conclude that ADK expression is necessary, but not sufficient for sensitivity to 6-ETI, and that ADK expression is associated with a cellular state that renders cells sensitive to 6-ETI. The inventors also synthesized the cyclical form of 6-ETI (c6-ETI), which requires cleavage within the cell to expose the phosphate. This compound was equally as effective in PEL and MM as the original 6-ETI as well as in colon and pancreatic adenocarcinoma cell lines.

To assess whether 6-ETI may be toxic to normal plasma cells, the inventors treated total tonsil B lymphocytes with 1 μM and 10 μM 6-ETI for 24 hours and subsequently gated for plasma cells (CD19−, CD138+). The inventors did not find a decrease in the total number or proportion of plasma cells (FIG. 6E) upon treatment, so it was concluded that while these express high levels of ADK they are not sensitive, likely because they are not proliferative.

Figures 7A, 7B:
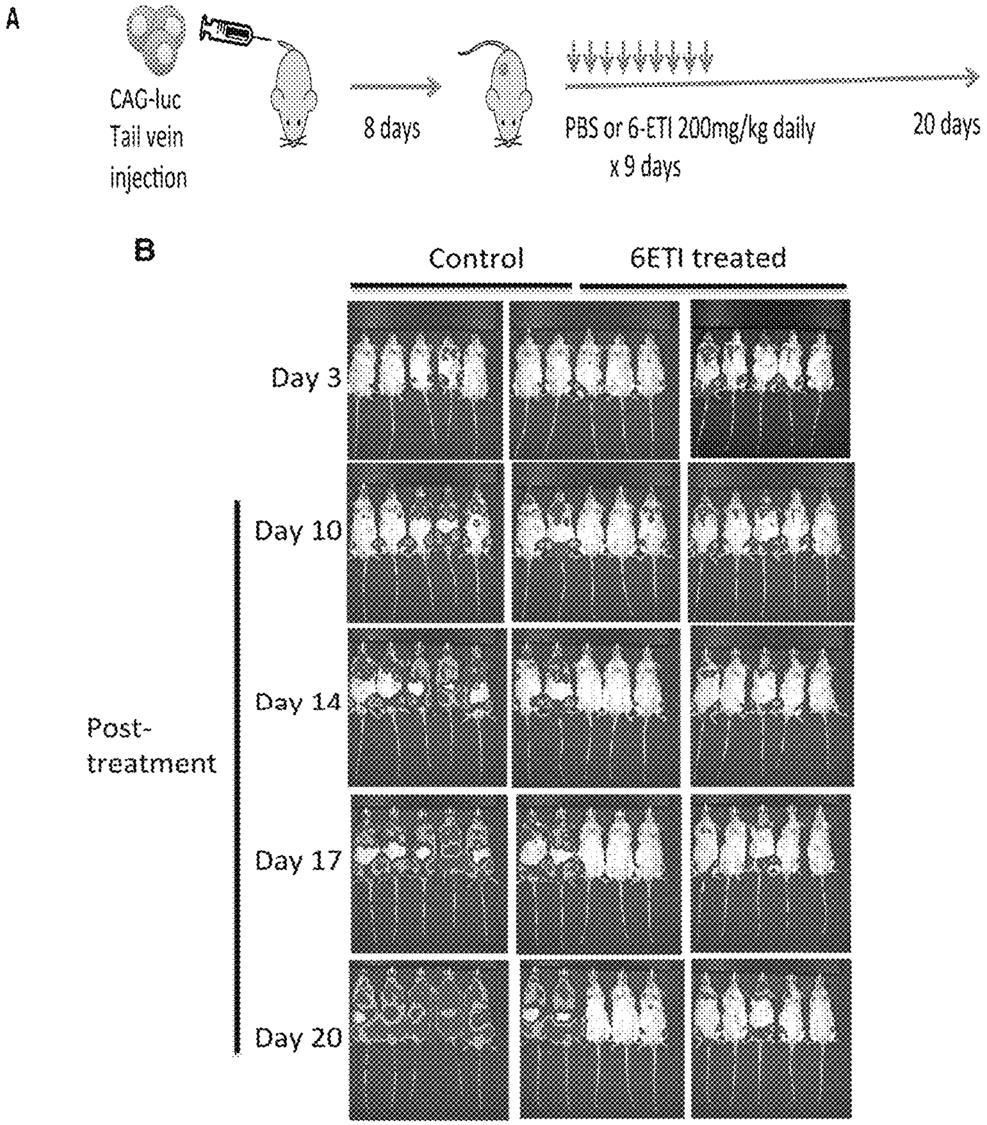
Figures 7C, 7D:
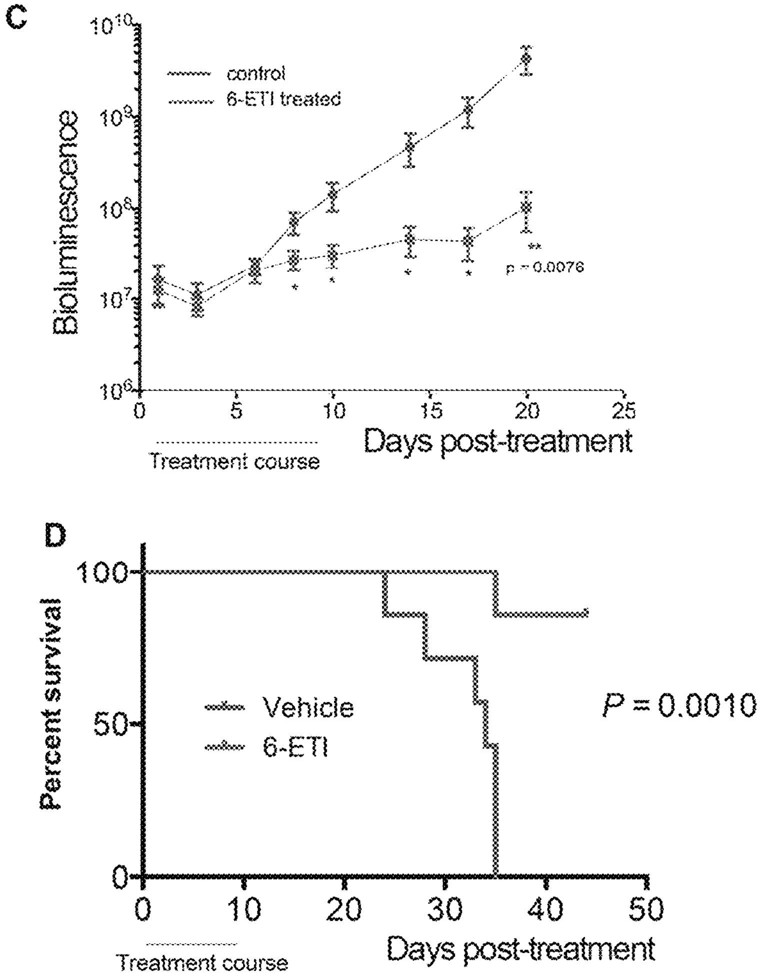

Example 13: Effectiveness of 6-ETI in a Disseminated Mouse Model of Multiple Myeloma Given the in vitro sensitivity data, the inventors also assessed the anti-tumor activity of 6-ETI in a disseminated MM xenograft model by intravenously injecting NOD/SCID mice with $Luc^+GFP^+$ CAG cells stably expressing the HSV-TK-eGFP-luciferase fusion protein. Prior to injection, it was confirmed that CAG-luc cells expressed monotypic cytoplasmic light chains and ADK. Anatomical distribution and pathophysiological manifestation of this model were compatible with the clinical course of MM in humans, i.e., hallmarked by malignant plasma cells present mainly within the bones (sternum, femur, tibia, vertebrae, skull, mandible) and associated with multifocal lytic bone lesions. The inventors monitored tumor burden by bioluminescence imaging. Seven mice were treated with vehicle, and eight with 200 mg/kg/day of 6-ETI (FIG. 7A). It was found that mice treated with 6-ETI had significant reduction in tumor burden as assessed by the bioluminescent signal (FIGS. 7B and 7C) without any weight loss. Moreover, overall survival was also significantly prolonged in the 6-ETI treated group compared to the control mice (FIG. 7D, $P<0.005$).

Example 14: Comparison with Other Nucleoside Analogues

The inventors tested whether the selectivity profile of 6-ETI to PEL and MM is unique or is a general feature of related nucleoside analogues. The inventors first tested 6-mercaptopurine/6-MP (Table 1). 6-ETI is structurally similar to 6-MP, but the latter lacks the ribose ring where phosphorylation occurs. Interestingly, 6-MP, while not particularly effective against PEL cells, demonstrated selectivity to them, much like 6-ETI, suggesting that it may be metabolized to an intermediate that may be phosphorylated by ADK, albeit with low efficiency (Table 1). The inventors also tested four different purine analogues that are FDA approved: vidarabine, didanosine, cladribine and fludarabine phosphate. None of these showed the same spectrum of selectivity or effectiveness towards PEL and MM as 6-ETI. To test if a pyrimidine analogue would have an effect towards PEL and MM, the inventors tested ribavirin. This drug has received recent attention for its effect on leukemias acting as a protein synthesis inhibitor, in addition to its antiviral effects (Borden K L. et al., *Clin Invest Med.* 2011; 34(6):E315). However, this drug had an effect on the viability of the two lymphoma lines tested only at very high concentrations ($LC_{50}$>44 μM) and even higher for multiple myeloma ($LC_{50}$>>100 μM) (Table 1).

Example 15: Adenocarcinomas Display Increased ADK Expression and 6-ETI Sensitivity The inventors have discovered that ADK is also highly expressed in adenocarcinomas, including those of colon, pancreas and lung. Expression has been documented by immunohistochemistry of diagnostic tissue specimens (FIG. 8A). In addition to the finding that colon adenocarcinomas express high levels of ADK, it was discovered that pre-malignant areas (with adenoma) were also positive, while normal colonic mucosa was not. It was also discovered that poorly differentiated colon cancer (medullary subtype), does not express ADK, again consistent with a role for ADK in differentiation. Similarly, a large proportion of lung adenocarcinoma and pancreatic adenocarcinomas expressed ADK, but not those with poor differentiation.

Correspondingly, a remarkable sensitivity to p6-ETI and c6-ETI was observed of cell lines corresponding to these tumors (FIG. 8B). This is an important finding, as they are common malignancies, and in particular pancreatic cancer is highly aggressive with few therapeutic options. Pyrimidine analogs like gemcitabine and capecitabine have been used for pancreatic cancer, but there is frequent resistance. Purine analogs have not been used for the treatment of adenocarcinomas. 6-ETI will provide an additional option to patients and has the added advantage of a clear biomarker that can be assessed by routine immunohistochemistry of the diagnostic biopsy.

Example 16: Cyclic 6-ETI (c6-ETI) and Phospho 6-ETI (p6-ETI) are Both Effective Against PEL Cells Cyclic 6-ETI (c6-ETI or 6-ETI cAMP) and phosphorylated 6-ETI (p6-ETI) were tested in a PEL xenograft model as shown in FIG. 9. It was found that both compounds effectively inhibited tumor growth in vivo (FIG. 9). In addition, it was also found that 6-ETI and its derivatives c6-ETI and p6-ETI showed similar sensitivity profiles in a variety of cell lines tested (colon cancer, PEL, MM, pancreatic cancer and diffuse large B cell lymphoma cell lines). Diffuse large B cell lymphomas were slightly more resistant to 6-ETI and 6-ETI derivatives, whereas all other cell lines displayed sensitivity to these drugs.

Example 17: Structure Activity Relationship Analysis Revealed Novel 6-ETI Derivatives that Retain Activity A panel of 6-ETI analog compounds (FIG. 10A) were tested and it was found that those with modification in the ribose ring retain activity (FIG. 10B), and a 6-methylthiol is also tolerated.

The inventors have also tested additions in the C8 position (i.e. 8-chloro, 6-thioethyl purine riboside and 8-bromo, 6-thioethyl purine riboside, etc.) with the chemical structure as following:

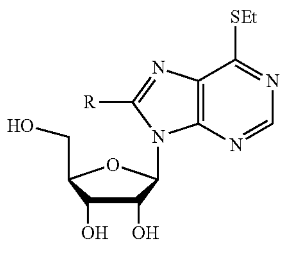

It was found that these modifications in C8 can be tolerated, albeit with higher $LC_{50}$ s. For instance, a Cl group at C8 position resulted in an $IC_{50}$ of 1410 nM, a $NH_2$ group at C8 position resulted in an $IC_{50}$ of 4484 nM, a Br group at C8 position resulted in an $IC_{50}$ of 8134 nM, and a $N_3$ group at C8 position resulted in an $IC_{50}$ of 1131 nM in a PEL cell line viability assay.

TABLE 1

Comparison of 6-ETI to other nucleoside analogs that are FDA approved, using of a PEL (BC3), a MM (U266), and an EBV+ DLBCL (IBL-1).

| Nucleoside analog tested | LC50 BC3 (PEL) in nM | LC50 U266 (MM) in nM | LC50 IBL-1 (DLBCL) in nM |
|---|---|---|---|
| 6-ETI | 49.79 | 437.35 | >>100 μM |
| Ribavirin | 44739 | >>>100 μM | 46487 |
| Vidarabine | >>100 μM | >>100 μM | >>100 μM |
| Didanosine | >>100 μM | >>100 μM | >>100 μM |
| 6-Mercaptopurine | 5143 | 10325 | >100 μM |
| Cladribine | 5237 | 29192 | 290.2 |
| Fludarabine | >>>100 μM | 90690 | 28853 |

Sensitivity after 48 hours or treatment is shown. Results shown are LC50s from viability assays (CellTiter-Glo) where the mean±SEM of two independent experiments performed in duplicates is provided.

What is claimed is:

1. A method of treating a subject having cancer of plasma cell origin or adenocarcinoma or a disease selected from the group consisting of Kaposi's Sarcoma (KS), multicentric Castleman's Disease (MCD), primary effusion lymphoma (PEL), diffuse large B-cell lymphomas, multiple myeloma, and plasmablastic lymphomas, the method comprising: (i) determining if the subject has an abnormally high level of expression of Adenosine Kinase (ADK) compared to cells or tissues of a healthy control subject; and (ii) if the subject is identified as having an abnormally high level of expression of ADK, administering to said subject an effective amount of a therapeutic compound, wherein the therapeutic compound has the following chemical structure:

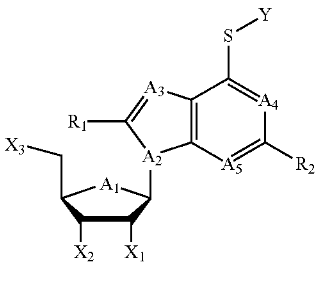

wherein:

$A_1$ is O;

$A_2$, $A_3$, $A_4$, and As are N;

Y is methyl or ethyl;

$R_1$ and $R_2$ are H;

$X_1$ and $X_2$ are independently selected from the group consisting of hydrogen, hydroxy, and acyloxy; and $X_3$ is selected from the group consisting of hydroxy, phosphate, acyloxy, and benzyloxy (BnO);

wherein, optionally, $X_1$ and $X_2$ are taken together to form a 1,3-dioxolane ring optionally substituted with methyl groups at the 2-position;

or, optionally, $X_2$ and $X_3$ are taken together to form a cyclic monophosphate.

2. The method of claim 1, wherein the subject has cancer of plasma cell origin or adenocarcinoma.

3. The method of claim 1, wherein the cancer of plasma cell origin is selected from the group consisting of primary effusion lymphoma (PEL), multiple myeloma (MM) and plasmablastic lymphoma (PBL).

4. The method of claim 1, wherein the adenocarcinoma is selected from the group consisting of pulmonary adenocarcinoma, adenocarcinoma of the colon, and pancreatic adenocarcinoma.

5. The method of claim 1, wherein subject has a disease selected from the group consisting of Kaposi's Sarcoma (KS), multicentric Castleman's Disease (MCD), and primary effusion lymphoma (PEL).

6. The method of claim 1, wherein the therapeutic compound has a chemical structure selected from any of the following:

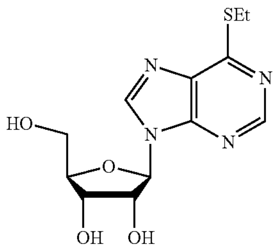

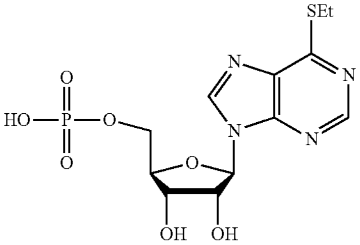

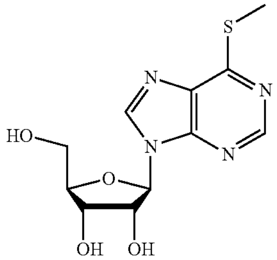

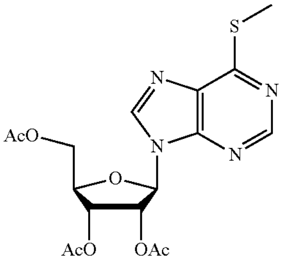

-continued

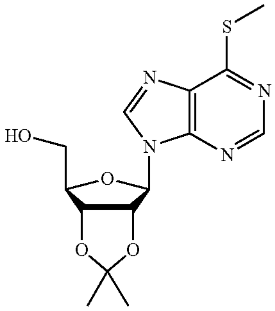

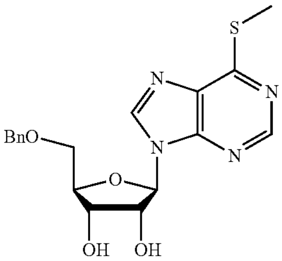

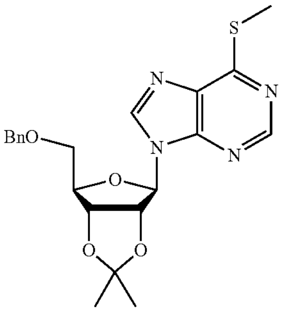

and

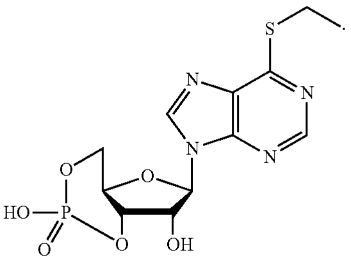

* * * * *